US008977019B2

(12) United States Patent
Chan et al.

(10) Patent No.: US 8,977,019 B2
(45) Date of Patent: Mar. 10, 2015

(54) METHODS FOR MICROCALCIFICATION DETECTION OF BREAST CANCER ON DIGITAL TOMOSYNTHESIS MAMMOGRAMS

(75) Inventors: Heang-Ping Chan, Ann Arbor, MI (US); Berkman Sahiner, Ann Arbor, MI (US); Lubomir M. Hadjiiski, Ann Arbor, MI (US); Jun Wei, Ann Arbor, MI (US); Mark A. Helvie, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/514,804

(22) PCT Filed: Feb. 11, 2011

(86) PCT No.: PCT/US2011/024469
§ 371 (c)(1),
(2), (4) Date: Jun. 8, 2012

(87) PCT Pub. No.: WO2011/100511
PCT Pub. Date: Aug. 18, 2011

(65) Prior Publication Data
US 2012/0294502 A1    Nov. 22, 2012

Related U.S. Application Data

(60) Provisional application No. 61/303,387, filed on Feb. 11, 2010.

(51) Int. Cl.
*G06K 9/00* (2006.01)
*G06T 7/00* (2006.01)
(Continued)

(52) U.S. Cl.
CPC .............. *G06T 7/0012* (2013.01); *A61B 6/025* (2013.01); *A61B 6/502* (2013.01); *A61B 6/5211* (2013.01); *G06T 2207/10112* (2013.01); *G06T 2207/30068* (2013.01)
USPC ........................................................ 382/128

(58) Field of Classification Search
None
See application file for complete search history.

(56) References Cited

U.S. PATENT DOCUMENTS 6,035,056 A * 3/2000 Karssemeijer ................ 382/132
6,075,879 A * 6/2000 Roehrig et al. ................ 382/132
(Continued)

OTHER PUBLICATIONS

Jinshan Tang, Rangaraj Rangayyan, Jun Xu, Issam Naga, Yongyi Yang. "Computer-Aided Detection and Diagnosis of Breast Cancer with Mammography: Recent Advances" IEEE , vol. 13 No. 2 . Mar. 2009.*

(Continued)

*Primary Examiner* — Jon Chang
*Assistant Examiner* — Oneal R Mistry
(74) *Attorney, Agent, or Firm* — Marshall, Gerstein & Borun LLP

(57) ABSTRACT

A computer-aided detection system to detect clustered microcalcifications in digital breast tomosynthesis (DBT) is disclosed. The system performs detection in 2D images and a reconstructed 3D volume. The system may include an initial prescreening of potential microcalcifications by using one or more 3D calcification response function (CRF) values modulated by an enhancement method to identify high response locations in the DBT volume as potential signals. Microcalcifications may be enhanced using a Multi-Channel Enhancement method. Locations detected using these methods can be identified and the potential microcalcifications may be extracted. The system may include object segmentation that uses region growing guided by the enhancement-modulated CRF values, gray level voxel values relative to a local background level, or the original DBT voxel values. False positives may be reduced by descriptors of characteristics of microcalcifications. Detected locations of clusters and a cluster significance rating of each cluster may be output and displayed.

19 Claims, 16 Drawing Sheets

(51) Int. Cl.
  *A61B 6/02* (2006.01)
  *A61B 6/00* (2006.01)

(56) References Cited

U.S. PATENT DOCUMENTS

| | | | | |
|---|---|---|---|---|
| 6,137,898 | A  * | 10/2000 | Broussard et al. | 382/132 |
| 6,205,236 | B1 * | 3/2001 | Rogers et al. | 382/132 |
| 6,801,645 | B1 * | 10/2004 | Collins et al. | 382/130 |
| 6,898,303 | B2 * | 5/2005 | Armato et al. | 382/131 |
| 7,218,766 | B2 * | 5/2007 | Eberhard et al. | 382/132 |
| 7,310,435 | B2 * | 12/2007 | Mallya et al. | 382/128 |
| 7,474,776 | B2 * | 1/2009 | Kaufman et al. | 382/128 |
| 7,853,064 | B2 * | 12/2010 | Bernard et al. | 382/132 |
| 8,041,094 | B2 * | 10/2011 | Bernard et al. | 382/131 |
| 8,260,014 | B2 * | 9/2012 | Chen et al. | 382/128 |
| 8,391,574 | B2 * | 3/2013 | Collins et al. | 382/128 |
| 2007/0286470 | A1 | 12/2007 | Bernard et al. | |
| 2008/0025592 | A1 | 1/2008 | Jerebko et al. | |
| 2009/0080752 | A1 | 3/2009 | Ruth et al. | |
| 2009/0232376 | A1 * | 9/2009 | Raundahl et al. | 382/131 |
| 2009/0297002 | A1 | 12/2009 | Zhang et al. | |

OTHER PUBLICATIONS

Matthias Elter, Alexander Horsch, "CADx of mammographic masses and clustered microcalcification: A Review" Med. Phys., vol. 36,. Jun. 2009.*

Tang et al., "Computer-Aided Detection and Diagnosis of Breast Cancer with Mammography: Recent Adances", IEEE vol. 13, No. Mar. 2009.*

International Search Report and Written Opinion for Application No. PCT/US2011/024469 dated Oct. 19, 2011.

* cited by examiner

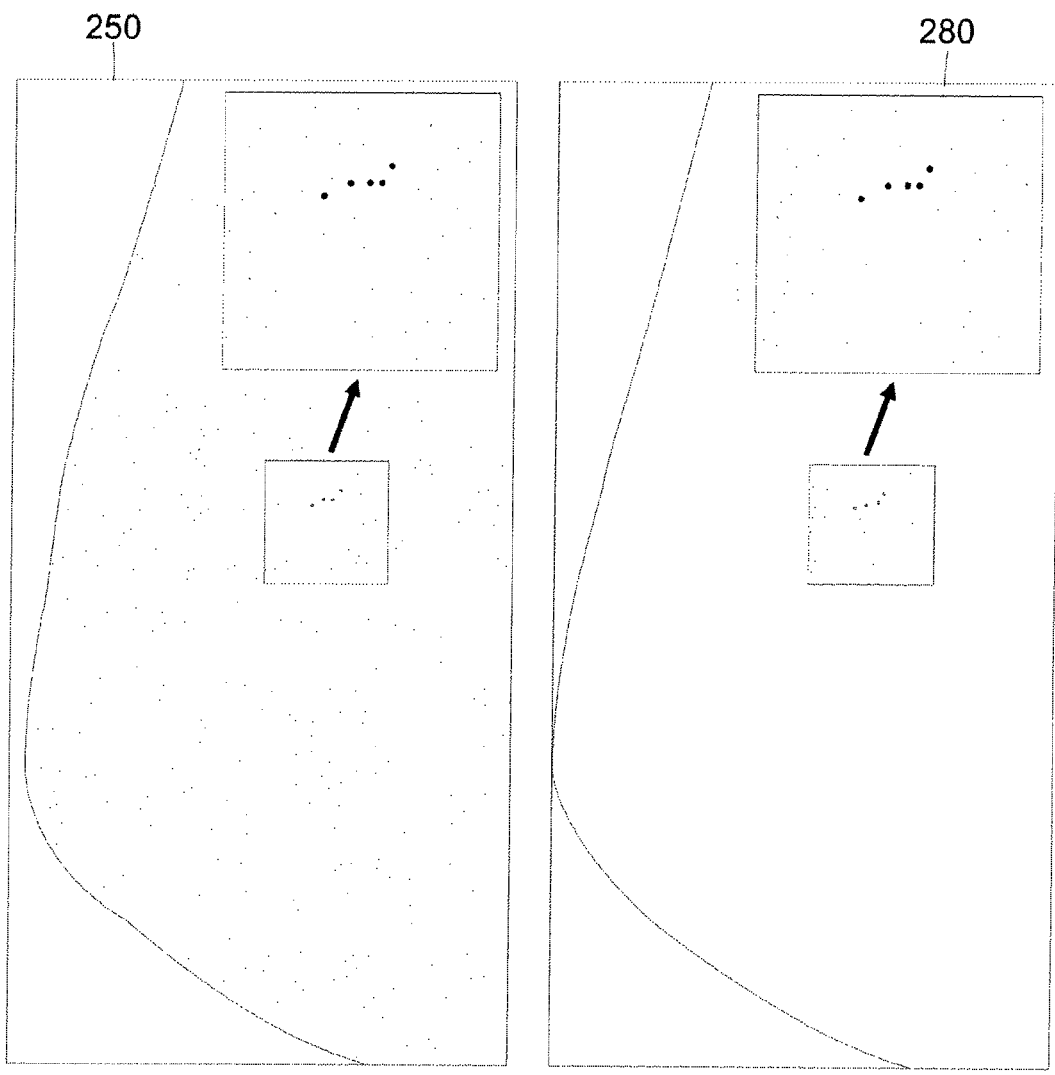

METHODS FOR MICROCALCIFICATION DETECTION OF BREAST CANCER ON DIGITAL TOMOSYNTHESIS MAMMOGRAMS

CROSS REFERENCE TO RELATED APPLICATION

This is a national phase of International Patent Application No. PCT/US2011/024469 filed Feb. 11, 2011, which in turn claims the priority benefit of the benefit of U.S. Provisional Application No. 61/303,387 filed Feb. 11, 2010, and are entirely incorporated by reference herein.

STATEMENT REGARDING FEDERALLY SPONSORED RESEARCH OR DEVELOPMENT

This invention was made with government support under CA120234 awarded by the National Institutes of Health. The government has certain rights in the invention.

FIELD OF TECHNOLOGY

This relates generally to breast cancer detection and, more particularly, to a system and method for using computer-aided detection (CAD) for clustered microcalcifications in Digital Breast Tomosynthesis (DBT).

DESCRIPTION OF THE RELATED ART

Breast cancer is one of the leading causes of death among American women between 40 and 55 years of age. There is considerable evidence that early diagnosis and treatment significantly improves the chance of survival for patients with breast cancer. Although mammography has a high sensitivity for detection of breast cancers when compared to other diagnostic modalities, studies indicate that radiologists do not detect all carcinomas that are visible upon retrospective analyses of the images. One major problem in screening mammography is the limited sensitivity in dense breasts, due to the camouflaging effect of overlapping dense tissue. Another problem in screening is the high recall rate of about 10%. Many of these recalls are caused by overlapping tissue mimicking a lesion. Finally, the specificity of screening mammography for differentiating lesions as malignant and benign is very low. In the United States, the positive predictive value of recommended biopsies ranges from about 15 to 30%. Recall and benign biopsies not only cause patient anxiety and morbidity, but also increase health care costs.

Dense fibroglandular parenchyma reduces the conspicuity of abnormalities on mammograms, which constitutes one of the main causes of missed cancer. A potential approach to reducing missed cancer is to include ultrasound (US) scans in screening exams of dense breasts. US scanning is time consuming and relatively operator-dependent and cannot detect microcalcifications (MCs). It may only be used as an adjunct to mammography for a selected patient population. Breast MR is expensive and has relatively low specificity, limiting its use to high-risk patients and diagnostic purposes.

The advent of high-resolution digital detectors has enabled the development of new techniques for reducing overlapping breast structures such as digital breast tomosynthesis (DBT), breast computed tomography, and stereomammography. The principle of tomosynthesis is the same as conventional tomography but digital imaging allows reconstruction of slices at any depth with a single scan, resulting in much lower dose and higher image quality. DBT is similar to mammography such that the breast is imaged under compression. A sequence of projection views (PVs) is acquired by the digital detector as the x-ray source is rotated to different angular positions about a fulcrum over a finite angular range (referred to as the tomo angle in the following). With a proper tomosynthesis reconstruction algorithm, tomographic slices focused at any depth can be generated from the PVs. Because of the wide dynamic range and the linear response of the digital detector, each PV can be acquired with a fraction of the exposure used for a regular mammogram. The total dose required for DBT may be kept at nearly the same as that of a regular mammogram. The in-plane resolution can approach that of the digital detector if the geometry of the scanning system is accurately known although some degree of blurring is inevitable due to the reconstruction from multiple PVs with different x-ray incident angle. DBT is a promising method that can improve sensitivity for breast cancer detection in general because it not only reduces the camouflaging effects of overlapping tissue but it improves the assessment of mass margins, thus facilitating the differentiation of normal tissue from subtle spiculated masses even in fatty breasts. Promising initial results have prompted full field digital mammography (FFDM) manufacturers to develop DBT systems. Currently, one manufacturer has FDA approval for their DBT system as an adjunct to mammography, and others are in the process of applying for FDA approval.

Important issues related to image quality and visibility of MCs, protocols for integrating DBT into screening (e.g., replacing FFDM, adding one or two DBT views to FFDM, etc), and the associated system design parameters, patient exposure, and radiologists' reading time are still at early stages of investigation, as discussed below.

DBT is basically a limited angle cone-beam computed tomography (CT) technique. Because of the lack of PVs at large angles, the spatial resolution in the direction perpendicular to the detector plane (the depth or Z-direction) is poor. The depth resolution is mainly determined by the tomo angle; the larger the angle, the higher the depth resolution and the less the interplane artifact. DBT is inferior to breast CT in terms of depth resolution and the need of compression. However, DBT has the following advantages over breast CT: (1) it has higher in-plane spatial resolution and requires less exposure, (2) it can be built upon the existing FFDM technology, and (3) the DBT slices are similar in appearance to FFDM except for the reduced complexity of overlapping tissue so that radiologists may more readily adapt to reading this new modality.

Other studies using prototype DBT systems have compared DBTs with mammography in breast cancer detection. Some compared the image quality of diagnostic film mammograms to DBT acquired with a Hologic prototype, and evaluated the effect of adding DBT to FFDM screening on the recall rate in subjects. They found that the recall rate could be reduced by 40% with the addition of DBT and the DBT image quality was equivalent or superior to the diagnostic mammogram in the vast majority of the cases but the conspicuity of MCs were inferior in many of the cases. Others compared lesion detection on FFDM to that on combined FFDM+DBT acquired by a Hologic prototype. They found that the combined FFDM+DBT reading improved the area under the ROC curve (AUC) for all radiologists and the mean recall rate decreased by about 39%. This improvement was gained at the cost of doubling the dose, however. Yet others conducted an observer study to compare 2-view FFDM alone to 2-view DBT alone and FFDM (2-view)+DBT(2-view) using a Hologic prototype. They found that DBT alone can reduce recall rate by about 10% while FFDM+DBT could reduce recall rate by 30% without a conclusive change in sensitivity due to the small number of cancers in their study. Still others performed an ROC study to compare lesion detection and characterization in 2-view FFDM with that in single mediolateral oblique (MLO)-view DBT from a GE prototype in 92 breasts. They found that the conspicuity of masses was significantly higher in DBT. They also found that the conspicuity of MCs was significantly higher in DBT when the MCs were displayed in a thick-slab mode. The AUC for BI-RADS assessment was higher in DBT than in FFDM for all radiologists.

Some studies collected two-view DBT using a GE prototype DBT system for subjects that were recommended for biopsy of breast masses to develop computerized analysis methods for masses.

In summary, studies to date indicate that while mass detection and characterization are consistently better in DBT than in regular mammograms, there are variations in the reported performance of MC assessment. Although the intra- and inter-observer variabilities and relatively small samples in these studies can be contributing factors, the differences may also result from a dependence of MC visibility on imaging parameters and characteristics of the prototype DBT systems, and the reconstruction and the display methods.

One of the major concerns of bringing DBT into clinical practice is the large number of reconstructed slices for each breast. Even at 1-mm slice thickness, the number of slices per view of the breast will range from about 30 to over 80. The time required for interpretation of a DBT case was shown to be substantially longer than that for mammograms. With the increase in radiologists' workload, the chance for oversight of subtle lesions may increase, especially for subtle MC clusters. The detection of microcalcification clusters by radiologists in DBT volumes may be more difficult compared to mammography for two reasons: First, the cluster of microcalcifications may be separated into several reconstructed slices, the number of microcalcifications on each slice will be fewer, making it less conspicuous. Second, the microcalcifications may appear blurred due to many factors that can cause blurring in DBT reconstruction, including inaccuracy in the system geometry and the projection model, a range of oblique incidence angles to the detector, focal spot motion and patient motion. Reliable computer-assisted reading of MCs is therefore critical to the adoption of DBT as a screening modality.

Computer-aided detection (CAD) in screening mammography has been introduced into clinical use for over 10 years. Studies to-date shows that CAD can improve radiologists' lesion detection sensitivity in retrospective studies and in prospective clinical trials but moderately reduce specificity due to its recommended use as a second reader. The prospective clinical trials in screening mammography reported an increase in cancer detection sensitivity ranging from 5% to 19%, accompanied with an increase in recall rate from 6% to 31%. It has been found that CAD has no significant effect on the radiologists in their academic setting when they averaged the results from both low-volume and high-volume radiologists. One study that had the largest number of mammography cases read with CAD to date compared 9 experienced radiologists' reading of 112,413 cases without CAD, and 118,808 cases with CAD. It was found that CAD increased breast cancer detection sensitivity by 11% with only a 3.9% increase in the recall rate. Another study estimated the change in average breast cancer detection and recall rates after implementation of CAD in seven screening facilities. It reported that the detection rate for in-situ cancers increased by 34%, while that for invasive cancers decreased by 12% with CAD, resulting in an overall increase in sensitivity of only 4.5% and an increase in the recall rate of 30.7%. The fact that their computer-aided readings seem to track the performance of the CAD systems, especially the reduced cancer rate for invasive cancers, raised an alarm that the participating radiologists might have over-relied on the CAD system and did not maintain their vigilance in the first read. The relatively short experience of some participants in using CAD (the shortest was 2 months) and not properly using CAD as a second reader in this study may have contributed to the higher recall rate.

A number of studies investigated the development of CAD techniques for the detection of masses in DBT. Compared to the detection of masses, studies investigating the detection of microcalcification clusters on DBT are more preliminary. Reiser et al. investigated the detection of microcalcifications on individual PVs. The detected microcalcifications were then backprojected into the 3D volume. A second-stage detection was performed after this 3D volume was transformed used MIP. False-positive reduction was performed with features extracted from PVs, followed by 3D clustering. On a data set of 30 image sets with microcalcification clusters and 30 image sets without visible findings, the method of Reiser et al. achieved a sensitivity of 86% with 1.3 FP clusters per DBT volume. Bernard et al. developed an algorithm for the detection of microcalcification clusters on filtered back-projection reconstructed slices. The voxel contrast was enhanced by convolving the image volume with a Mexican hat wavelet at a specific scale. A voxel was selected as a candidate based on its contrast and the local noise level. A set of scales covering the microcalcification size range was used for the Mexican hat. On a data set of 13 DBT volumes containing microcalcification clusters and 37 normal DBT volumes, the method of Bernard et al. had a sensitivity of 85% at an average of 1.4 FP marks per breast volume. Park et al. compared two preliminary detection methods. The first method detected microcalcification clusters on the individual PVs, and the second method detected clusters on the individual reconstructed slices. Both methods then grouped the detected clusters using location information. The first method detected 14 of 20 (70%) clusters seen on the PV images with an average of 3.99 FPs per DBT volume. The second method detected 35 of 40 (86%) of clusters seen on the reconstructed slices with an average of 15.9 FPs per DBT volume. The performance of these preliminary MC detection systems and methods are far from being practical for clinical use.

There is thus a need to develop an integrated practical approach to resolving the MC visualization and detection problems in DBT without increasing patient exposure.

Thus, to recap, computer-aided detection (CAD) can improve radiologists' sensitivity for breast cancer detection in mammography. Although the conspicuity of masses may be improved in DBT, the chance of oversight may not be negligible because of the large number of images in a DBT volume. In addition, the visibility of microcalcifications may be reduced, because of the separation of microcalcifications in a cluster into different slices, increased noise associated with multiple low-dose projection view acquisition, and potential blurring and artifacts arising from the tomosynthesis reconstruction, thereby making microcalcifications more subtle and difficult to visualize. Computer-aided detection (CAD) may therefore play an important role in DBT interpretation.

SUMMARY

Digital breast tomosynthesis (DBT) mammography is a promising modality that has the potential to improve breast cancer detection, especially in dense breasts. A computer-aided detection (CAD) system for clustered microcalcifications in DBT is disclosed. The microcalcification CAD system performs detection in a reconstructed 3D volume. A plurality of DBT slices can be generated from projection views (PVs) by any of a number of possible reconstruction methods known to those of ordinary skill in the art. The detection system may include an initial prescreening of potential microcalcifications by using one or more 3D calcification response function (CRF) values modulated by a signal or a signal-to-noise (SNR) enhancement filter to identify high response locations in the DBT volume as potential signals. The prescreening may also include the detection of peaks in an SNR-enhanced volume. Locations detected using both of these two parallel methods can be identified, and the SNR may be extracted for the signals at these locations. The detection system may also include object segmentation that uses 3D region growing that may be guided by the enhancement-modulated CRF values, the SNR values, a plurality of gray level voxel values relative to a local background level, or the original DBT voxel values. Features that describe the SNR, morphological and gray level characteristics of the segmented objects may be extracted to differentiate true and false microcalcifications. 3D dynamic clustering may then be performed to identify microcalcification clusters using hierarchical criteria, such as, for example, the proximity of the cluster members, the enhancement-modulated CRF value, and other feature descriptors to determine the cluster membership. The features of the potential clusters may then be further analyzed using the 3D image information extracted from the DBT volumes and 2D image information extracted from the PV images before reconstruction. The 3D or the combined 3D and 2D analysis may provide a microcalcification likelihood score for each potential cluster or the individual microcalcification candidates, which can be used as a decision variable to select the most suspicious clusters to be displayed to a radiologist.

Microcalcification clusters may be detected in the reconstructed DBT volume using a combined 3D calcification response enhancement and SNR enhancement. On a data set of two-view DBTs containing microcalcification clusters, a view-based sensitivity of approximately 80% or greater may be achieved at 2.0 FPs per DBT volume. Microcalcification detection may be further improved by optimizing the SNR enhancement-modulated CRF as well as clustering compared to using SNR enhancement alone.

A CAD system may detect microcalcification clusters in reconstructed volumes of DBT 3D images. A method using the CAD system to detect microcalcification may generally include three stages: prescreening, clustering, and false-positive reduction. In the prescreening stage, the conspicuity of microcalcification-like objects may be increased by an enhancement-modulated 3D calcification response function. An iterative thresholding and 3D object growing method may then be used to detect seed objects. In the cluster detection stage, a second iterative thresholding procedure may be used to identify microcalcification candidates with a positive calcification response in the SNR-enhanced volume. Starting with each seed object as the initial cluster center, a dynamic clustering algorithm may form a cluster candidate by including microcalcification candidates within a 3D neighborhood of the seed object that satisfied the clustering criteria. The number, size, and SNR of microcalcifications in a cluster candidate and the cluster shape may be used to reduce the number of false-positives (FPs).

Using this system, the prescreening stage may detect a seed object in biopsied microcalcification clusters at a threshold of 100 seed objects per DBT volume. After clustering, the number of detected clusters may be reduced to 15 marks per DBT volume. The FP reduction stage may further reduce the number of FPs per DBT volume and the cluster detection sensitivity will depend on the decision threshold setting.

BRIEF DESCRIPTION OF DRAWINGS

FIG. 2c is an illustration of an exemplary DBT slice containing a microcalcification cluster that has been enhanced by a 3D calcification response function;

FIG. 2d is an illustration of an exemplary DBT slice containing a microcalcification cluster that has been enhanced by the enhancement-modulated calcification response (EMCR);

DETAILED DESCRIPTION

Figure 1:
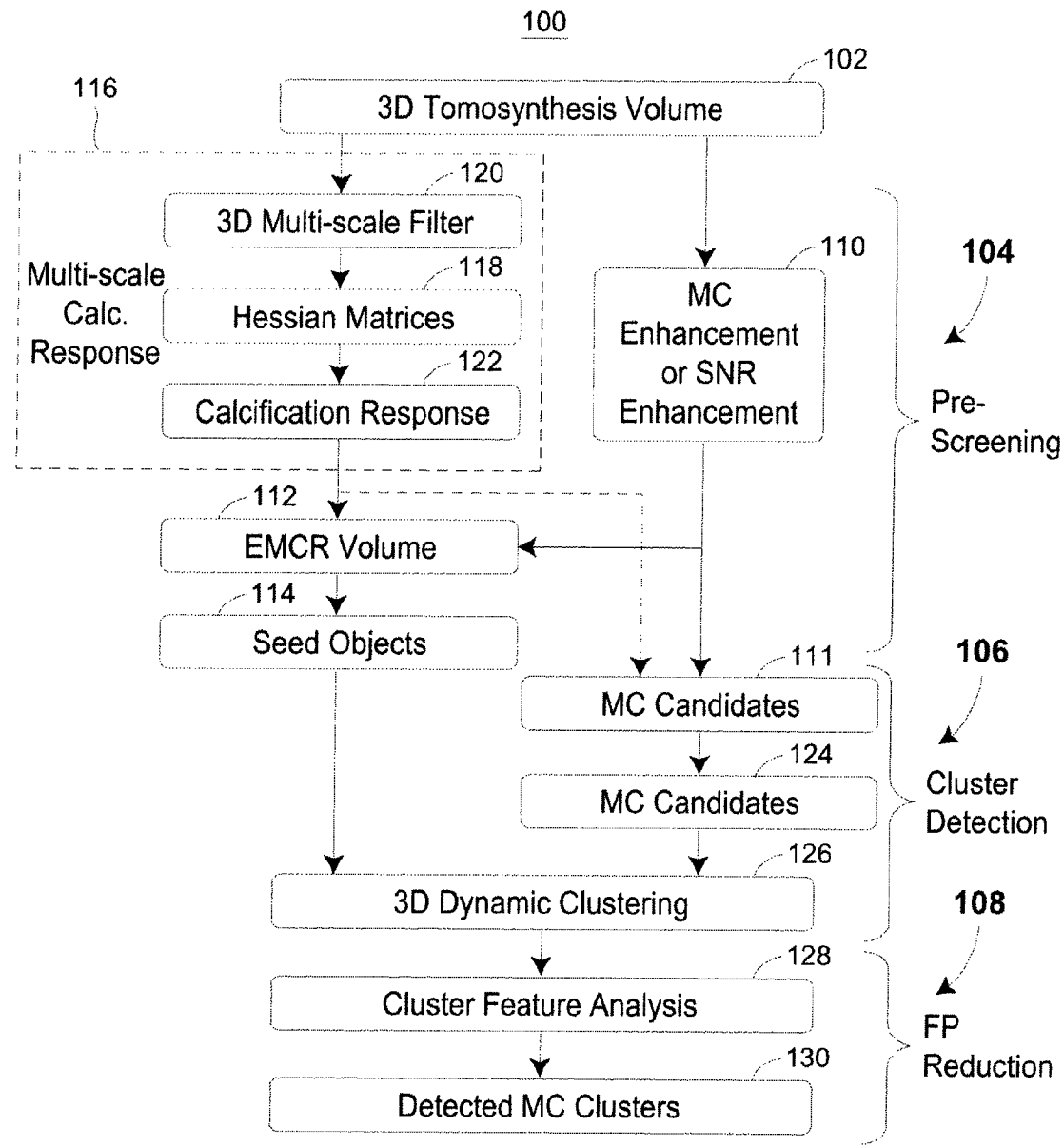
FIG. 1 is an exemplary flow chart of several blocks in a microcalcification detection system for DBT.

FIG. 1 discloses an exemplary flow chart of a computer-aided detection (CAD) method 100 for clustered microcalcifications in digital breast tomosynthesis (DBT). The method may begin with generation or collection of a plurality of DBT mammograms using a DBT mammography system. The DBT system may acquire, for example, 11 to 25 PVs over an arc of 15 to 60 degrees in various increments (e.g., 3 degree increments). The DBT system may use a full-field digital detector, for example, a CsI/a-Si flat-panel or an amorphous-Se flat panel detector. The digital detector may be stationary or moving during image acquisition. The breasts may be imaged in either the craniocaudal (CC), mediolateral oblique (MLO), or other views. The DBT volumes may be reconstructed at a 1-mm-thick or other slice interval using a simultaneous algebraic reconstruction technique (SART) or other tomosynthesis reconstruction technique.

With reference to FIG. 1, a method 100 uses the tomosynthesized DBT slices of a 3D DBT volume 102 as inputs and image processing is performed in the 3D volume 102. FIG. 1 shows a block diagram of the CAD method 100, which consists of prescreening 104, cluster detection 106, and false-positive reduction stages 108. The details of each stage of the CAD system are described below.

A microcalcification cluster detection method and system may employ a 3D approach in which the reconstructed 3D DBT volume is used as input. FIG. 1 shows a block diagram of the CAD method and system. In some embodiments, the method and system 100 may include software modules and hardware modules for prescreening 104, cluster detection 106, and false-positive reduction 108 stages. The details of each stage of the CAD system are described below.

The various modules may be implemented as computer-readable storage memories containing computer-readable instructions (i.e., software) for execution by a processor of a computer system. The modules may perform the various tasks associated with detecting microcalcification clusters as herein described. The method and system 100 also includes both hardware and software applications, as well as various data communications channels for communicating data between the various hardware and software components.

As used herein, the terms "module" and "routine" refer to computer program logic used to provide the specified functionality. Thus, a module or a routine can be implemented in hardware, firmware, and/or software. In one embodiment, program modules and routines are stored in mass storage memory, loaded into system memory, and executed by a processor or can be provided from computer program products that are stored in tangible computer-readable storage media(e.g. RAM, hard disk, optical/magnetic media, etc.).

I. Prescreening

In the prescreening stage 104, the microcalcifications in a 3D Tomosynthesis Volume 102 may be enhanced using two parallel processes: one process may be based on multi-scale Hessian enhancement with a calcification response function 116, and the other may generally increase the visibility of a microcalcification object in a reconstructed DBT volume 110. For example, one function to increase the visibility of an MC object may be based on SNR enhancement of the microcalcifications in the reconstructed DBT volume and another function may be based on enhancement of the signal strength of the microcalcifications (MC). At 112, the resulting enhanced calcification response volume may be weighted by the SNR-enhanced or MC-enhanced volume to obtain the enhancement-modulated calcification response (EMCR) function at each voxel. At 114, a threshold may be applied to the EMCR to identify seed objects for microcalcification clusters.

A. Multi-Scale Calcification Response

The multi-scale calcification response function, method or module 116 may be adapted to detect small bright objects in a DBT image. It may be based on the principle that at the center of a spherically symmetric object with positive contrast, the eigenvalues of the Hessian matrix 118 are all negative and equal to each other. At voxels that are part of other kinds of shapes (i.e., at voxels that are part of lines or elongated ellipses), the Hessian matrix 118 will have unequal eigenvalues. In practice, to reduce the noise that may be amplified by the second-order derivatives in the Hessian operator, the image I(x, y, z) may be first convolved with a 3D Gaussian-shaped smoothing filter 120, as described by the following equations:

$$s_\sigma(x, y, z) = \exp\{-(x^2+y^2+z^2)/2\sigma^2\} \quad \text{(Equation 1)}$$

Let f(x, y, z) denote the smoothed image volume, $$H_\sigma(x, y, z) = \begin{bmatrix} f_{xx} & f_{xy} & f_{xz} \\ f_{yx} & f_{yy} & f_{yz} \\ f_{zx} & f_{xy} & f_{zz} \end{bmatrix} \quad \text{(Equation 2)}$$

denote the Hessian matrix 118 at a voxel (x,y,z) of the smoothed volume, and $$|\lambda_3| \le |\lambda_2| \le |\lambda_1| \quad \text{(Equation 3)}$$

denote the eigenvalues of the Hessian matrix 118 at (x,y,z). At 122, a module to enhance a spherically-symmetric object may define a calcification response 122 "r" at scale σ as $$r_\sigma = \begin{cases} -\lambda_3^2/\lambda_1 & \text{if } \lambda_1 \le \lambda_2 \le \lambda_3 \le 0 \\ 0 & \text{otherwise} \end{cases} \quad \text{(Equation 4)}$$

If the object has a Gaussian shape with $$I(x, y, z) = \exp\{-(x^2+y^2+z^2)/2\sigma_0^2\} \quad \text{(Equation 5)}$$

then it can be shown that among all possible scales for the filter 120 $s_\sigma(x, y, z)$, the scale $$\sigma' = \sqrt{3/2}\sigma_0 \quad \text{(Equation 6)}$$

maximizes $r_\sigma$. In general, the size of the object 114 may be unknown and its shape may not be spherical. A common approach in this case may be to use a bank of Hessian filters $S = \{s_{\sigma_1}, s_{\sigma_2}, \ldots, s_{\sigma_N}\}$ at multiple scales $\{\sigma\} = \{\sigma_1, \sigma_2, \ldots, \sigma_N\}$. A response vector $R = \{r_{\sigma_1}, r_{\sigma_2}, \ldots, r_{\sigma_N}\}$ may be obtained at (x,y,z), and the elements of R combined to achieve the desired signal enhancement. In one embodiment, a neural network may be used to combine the elements of R. In another embodiment:

$$i^* = \underset{i}{\operatorname{argmax}}\{r_{\sigma_i}\} \quad \text{(Equation 7)}$$

The multi-scale calcification response at (x,y,z) may then be defined as:

$$E(x, y, z) = \frac{r_{\sigma_{i^*}}}{\sigma_{i^*}} \quad \text{(Equation 8)}$$

The above method is different from past methods using a Hessian multi-scale method to enhance dot-type shaped objects. For example, in a method described by Li et al. "Selective enhancement filters for nodules, vessels, and airway walls in two- and three-dimensional CT scans," Medical Physics 30, 2040-2051, 2003, the image was convolved with a normalized Gaussian function:

$$s'_\sigma(x, y, z) = \frac{1}{(2\pi\sigma^2)^{3/2}} \exp\{-(x^2 + y^2 + z^2)/2\sigma^2\}$$

(different from equation 1, above) and after finding the response $r'_{\sigma_i}$ at each scale, each pixel value is multiplied by $\sigma_i^3$. The final output is then $$\max_{i=1,...\sigma_N} \{r'_{\sigma_i} \sigma_i^3\}.$$

This final output is different from Equation 8, above.

B. SNR Enhancement

SNR enhancement 110 may be applied to each slice 102 independently or the 3D DBT volume 102. The SNR enhancement and module 110 may be a combination of three filters, $F_1$, $F_2$, and $F_3$, of sizes $M_1 \times M_1$, $M_2 \times M_2$, and $M_3 \times M_3$, respectively, where $M_1 > M_2 \geq M_3$. The filters may be linear or non-linear. If linear, the filters may be combined to produce a single band-pass filter before convolution with the image to reduce processing time. The kernels of the filters may be centered at the calcification candidate. The difference of the filters $F_1$ and $F_2$, i.e., $F_1 - F_2$, may be designed to estimate the background image intensity around the calcification candidate, such that $M_1$ may be large enough to include the background, and $M_2$ may be large enough so that the microcalcification signal is excluded from the background estimation. The filter $F_3$ may be used to estimate or increase the average signal intensity for the microcalcification candidate, depending on the selection of $M_3$. SNR enhancement 110 may then be accomplished by convolving the combined band-pass filter with the DBT volume:

$$F(x, y, z) = F_3(x, y, z) - [F_1(x, y, z) - F_2(x, y, z)]. \quad \text{(Equation 9)}$$

Of course, other types of filters may be used for $F_1$, $F_2$, and $F_3$ such as boxcar filters, and Gaussian filters with appropriate kernels.

C. Seed Object Detection

The EMCR volume 112 may be defined as the voxel-by-voxel weighting of the multi-scale calcification response volume 122 by the SNR-enhanced or MC-enhanced volume 110

$$\text{EMCR}(x, y, z) = E(x, y, z) * [I(x, y, z) \otimes F(x, y, z)] \quad \text{(Equation 10)}$$

where $I(x, y, z) \otimes F(x, y, z)$ denotes the SNR-enhanced or MC-enhanced volume 110.

Figures 2A, 2B:
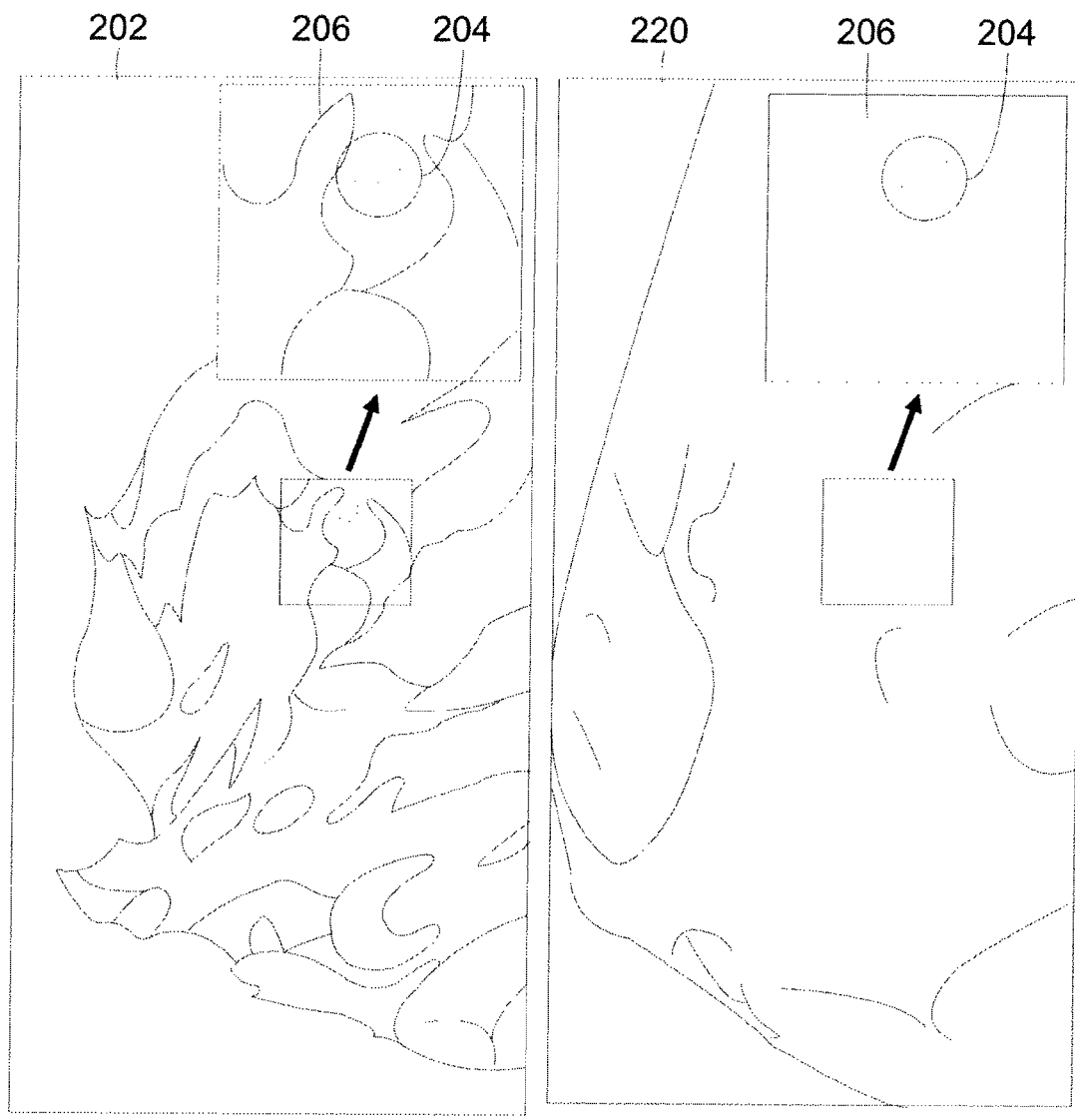
FIG. 2a is an illustration of an exemplary DBT slice containing a microcalcification cluster.
FIG. 2b is an illustration of an exemplary DBT slice containing a microcalcification cluster that has been enhanced for signal-to-noise ratio.

FIG. 2a illustrates a slice of a DBT volume 202 containing a microcalcification cluster 204 which was biopsy-proven to be ductal carcinoma in-situ. The image is shown as an example to demonstrate the methods and systems described herein. FIG. 2b illustrates an SNR-enhanced DBT slice 220, FIG. 2c illustrates a calcification response DBT slice 250, and FIG. 2d illustrates an EMCR image 280 of the same slice 202.

FIG. 2d (the EMCR volume) illustrates one result of an iterative thresholding and object growing technique designed to detect at least five hundred initial objects. The EMCR technique may start with a high enough initial threshold so that only a few connected objects would be initially detected. Voxels that were above the initial threshold may be marked and grouped into 3D connected objects using 26-connectivity. The threshold may then iteratively decreased until the number of connected objects is at least five hundred. For each detected initial object, the voxel with the highest EMCR value may be defined as the initial seed point.

In the early stage of development, some embodiments found that these initial objects 204 included small, nodular densities in the breast. The sizes of these densities were larger than those of most microcalcifications, and the transition from the density to the background was smoother than that for microcalcifications. To reduce the number of detected nodular densities, the initial objects in the original image volume may be segmented using a maximum-gradient object growing method. Starting with the initial seed point, the object may be segmented in a local region of the original DBT reconstruction volume using a multiple thresholding method. The maximum threshold may be equal to the largest voxel value in the local 3D region. In some embodiments, the threshold was lowered from this maximum value in fifty equal-sized steps. At each threshold value, the 3D connected object attached to the initial seed point was extracted, and the average radial gradient magnitude around the object resulting from the particular threshold was calculated. The object with the highest average radial gradient magnitude may be retained as the final segmented object. Objects with a volume larger than a predefined threshold $\text{Vol}_{max}$ (for example, 0.25 may be eliminated. The remaining objects are referred to as seed objects below.

II. Cluster Detection

In some embodiments, the seed objects are used as potential cluster centers in the clustering algorithm 106. To detect potential individual microcalcifications within a cluster 204, a second iterative thresholding and object growing procedure may be applied to the image. This second procedure may be similar to the procedure described above, but applied to the SNR-enhanced volume 220 (FIG. 2b). In the object growing process, any voxel that has a zero value for the multi-scale calcification response volume (as described by Equations 4 and 8) may be excluded. The threshold may then be reduced iteratively until a number of individual microcalcification candidates are detected in the volume. In some embodiments, the threshold is reduced until at least five-thousand individual microcalcification candidates are detected in the volume. The final threshold determined above may be described as the global object detection threshold.

At module 124, the SNR around each individual microcalcification candidate may be estimated using the MC-enhanced or SNR-enhanced volume 220. All voxel grayscale values referred to herein are values in the SNR-enhanced volume 220. For example, let $\text{Loc}_{max}$ denote the (x, y, z) location of the voxel with the highest grayscale value within a segmented seed object. The background region around $\text{Loc}_{max}$ may be defined as a 5×5×5 mm cube 206 centered at $\text{Loc}_{max}$ with voxels that had values less than the global object detection threshold. The average of the background voxels was calculated and subtracted from the grayscale value at $\text{Loc}_{max}$ to define the signal level. The SNR of the microcalcification candidate may then be found as the ratio of the signal level to the standard deviation of the background voxels. In addition, the size of the microcalcification candidate centered at $\text{Loc}_{max}$ may be estimated by thresholding the SNR at voxels in the vicinity of $\text{Loc}_{max}$. An SNR threshold of 3.0 may be used for including a voxel in the microcalcification candidate, although other thresholds may be used.

At module 126, a dynamic clustering algorithm may be used to detect a cluster candidate containing a seed object 114 starting with the seed object detected in the prescreening stage 104. Note that although a number of individual microcalcification candidates may be detected as described above, in some embodiments, clustering 126 is performed only around the seed objects 114 defined in the prescreening stage 104. Microcalcification candidates 111 may be ranked with respect to their SNR, and sequentially included in the cluster candidate following their rank order. For example, the MC candidate 111 may be included in the cluster candidate produced by the module 126 if the SNR of the MC candidate 111 exceeded an SNR threshold (e.g., an SNR threshold of 3.0 or other value), and if the MC candidate 111 was within a threshold radius of the cluster center (e.g., a 5 mm radius). After the inclusion of each individual microcalcification candidate 111, the cluster center may be updated as the centroid of all individual microcalcification locations within the cluster. Individual microcalcification candidates 111 included in the candidate cluster may then be marked to be excluded from other candidate clusters.

III. False-Positive Reduction

Particular characteristics of the MC candidates 111 and candidate clusters produced by the module 126 may be used to reduce the number of likely false-positives by a cluster feature analysis module 128 to produce a number of detected MC clusters 130. In some embodiments, the MC candidates 111 are chosen that are larger than a threshold value for SNR and are within a threshold size. For example, MC candidates 111 and clusters may be selected that have a minimum of four individual microcalcifications 111 (including the seed object) each with an SNR of at least 3.5 as the threshold criterion to be a member of a cluster candidate. Of course, other threshold values may be used. Within that cluster, each MC candidate 111 may be larger than a threshold size (e.g., seven voxels or more). However, if the cluster contains fewer than four MC candidates 111, then the cluster may be disregarded, unless the cluster includes more than ten individual MC candidates 111, regardless of size. Using thresholds to reduce the number of MC candidates 111 and clusters may eliminate false-positive clusters with a large number of small objects that are caused by image noise. However, since some clusters may consist of a large number of tiny microcalcifications 111, a threshold (e.g., more than ten individual microcalcifications) may be used. The 3D bounding boxes of the clusters may also be examined for false-positive reduction. The width and height of the cluster may be defined as the two dimensions of the bounding box in the plane parallel to the detector, while depth may be defined as the same dimensions, but in the perpendicular direction. Linear artifacts may also be eliminated as false-positives by imposing size thresholds. For example, a width or height less than a certain length (e.g., 2 mm) may be considered to be an indication of a linear artifact, and, thus, eliminated.

IV. Performance Evaluation

To evaluate the techniques described herein, tests may be performed to select parameters for prescreening. At pre-screening, a free-response receiver operating characteristic (FROC) curve may be used to evaluate the performance of that stage. Alternatively, the seed objects detected with the prescreening method described above may be examined. For example, the seed objects may be examined to determine whether they are inside the calcification bounding box provided by an experienced radiologist (i.e., whether a seed object was a true-positive (TP), or a false-positive (FP)). Further, a ranking of the EMCR value within TP objects may be used to assess the quality of the chosen parameters. For example, each object may be examined to determine the highest EMCR value in each object, and that value may be ranked for each DBT volume. The fraction of clusters $\mathcal{S}$ in the data set that would have included a seed point if objects with a rank of $\mathcal{R}$ or better are retained as detected object may also be examined. These ($\mathcal{R}$, $\mathcal{S}$) pairs may then be plotted in a way similar to an FROC curve (i.e., rank-sensitivity plots).

An overall performance of the detection system, including clustering and FP reduction, may be evaluated using FROC analysis. For FROC analysis, the highest SNR value within a detected cluster may be used as the decision variable. The detected cluster may be considered to be a true-positive if its centroid is within the 3D ground-truth box determined by the radiologist. Otherwise, the detected cluster may be considered a false-positive. Separate FROC curves may be constructed for malignant, benign, and all calcification clusters.

A. Effect of the Hessian Response Function Parameters

Figure 3:
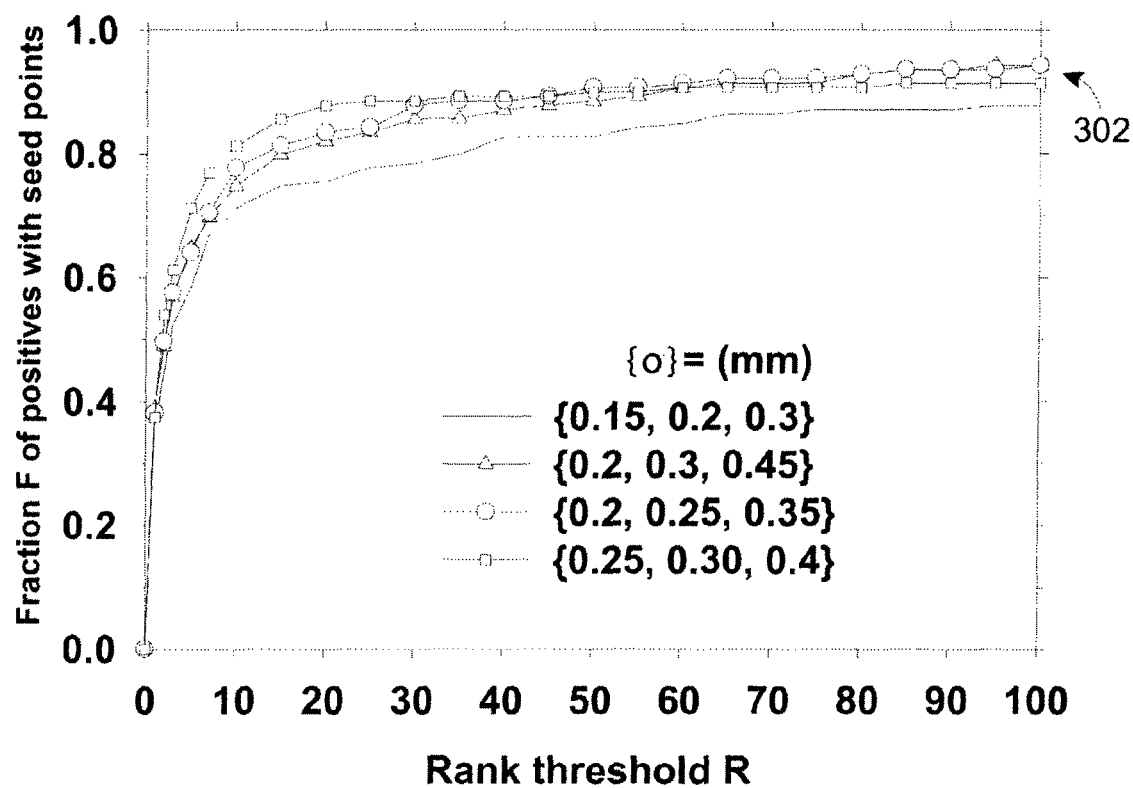
FIG. 3 is an illustration of a graph depicting an example of the effect of changes to the size of Hessian multi-scale filters on prescreening performance in a method and system to detect microcalcification clusters in DBT volumes.

As discussed above, a bank of Gaussian filters S corresponding to a set of scales $\{\sigma\}=\{\sigma_1, \sigma_2, \ldots, \sigma_N\}$ may be used for multi-scale Hessian response function. The effect of the scales on the calcification response may be evaluated. The number of scales may be selected as N=3. The scale of the Gaussian filter may be varied. In some embodiments, the scale of the Gaussian filter is varied between $\sigma$=0.15 mm and 0.45 mm, with various combinations of the scales to constitute the bank of filters S. Further, the SNR enhancement filter may be fixed at $M_1$=0.7 mm, $M_2$=0.1 mm, and $M_3$=0.1 mm. The rank-sensitivity plots are illustrated in FIG. 3. Based on these results, the set of scales may be selected as $\{\sigma\}\{0.2$ mm, 0.25 mm, 0.35 mm$\}$ in some embodiments.

B. Effect of the SNR Enhancement Filter Parameters

Figure 4:
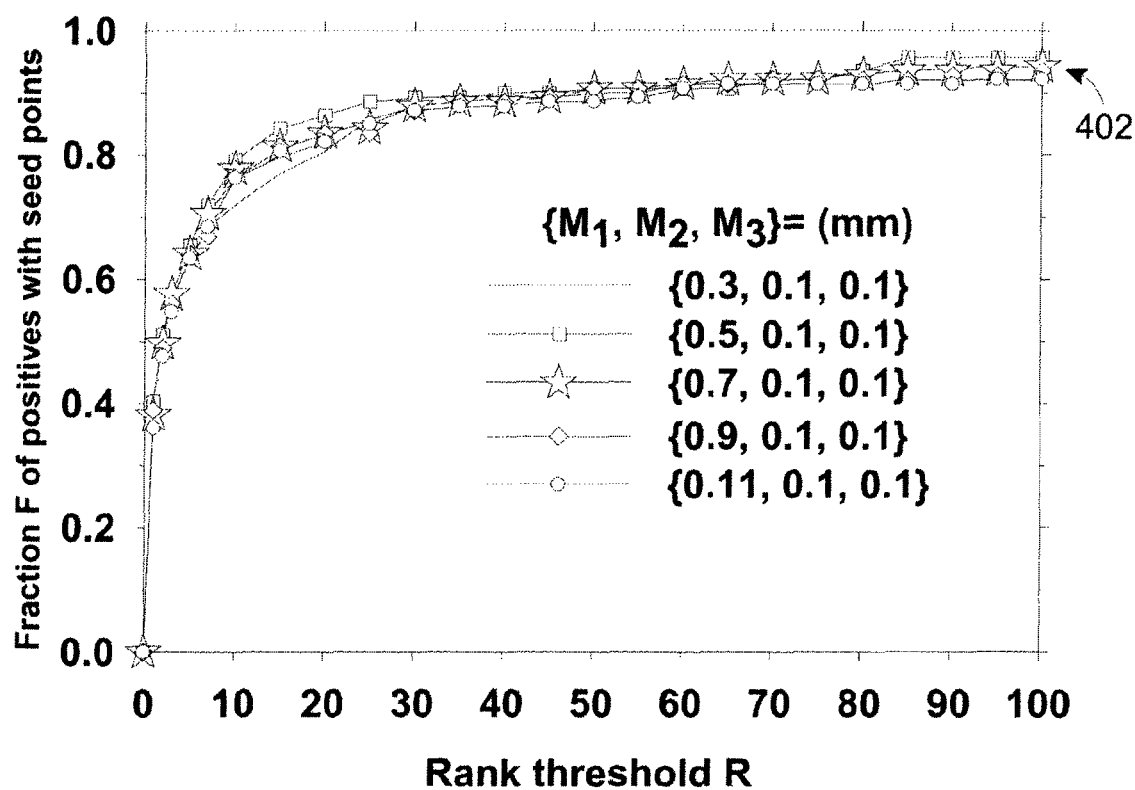
FIG. 4 is an illustration of a graph depicting an example of the effect of changes to the size of the outer filter kernel ($M_1$) on prescreening performance in a method and system to detect microcalcification clusters in DBT volumes.

To investigate the effect of SNR enhancement filter parameters, $M_1$ may be changed in the range of 0.3 mm to 1.1 mm. The other two filters may be fixed to $M_2$=$M_3$=0.1 mm, and the Hessian multi-scale filters may be set to $\{\sigma\}=\{0.20$ mm, 0.25 mm, 0.35 mm$\}$. The resulting rank-sensitivity plots are illustrated in FIG. 4. As shown, a small background area, $M_1$=0.3, may result in a slightly poorer performance (compared to FIG. 3), while other values of $M_1$ may lead to rank-sensitivity curves that are similar to FIG. 3.

Figure 5A:
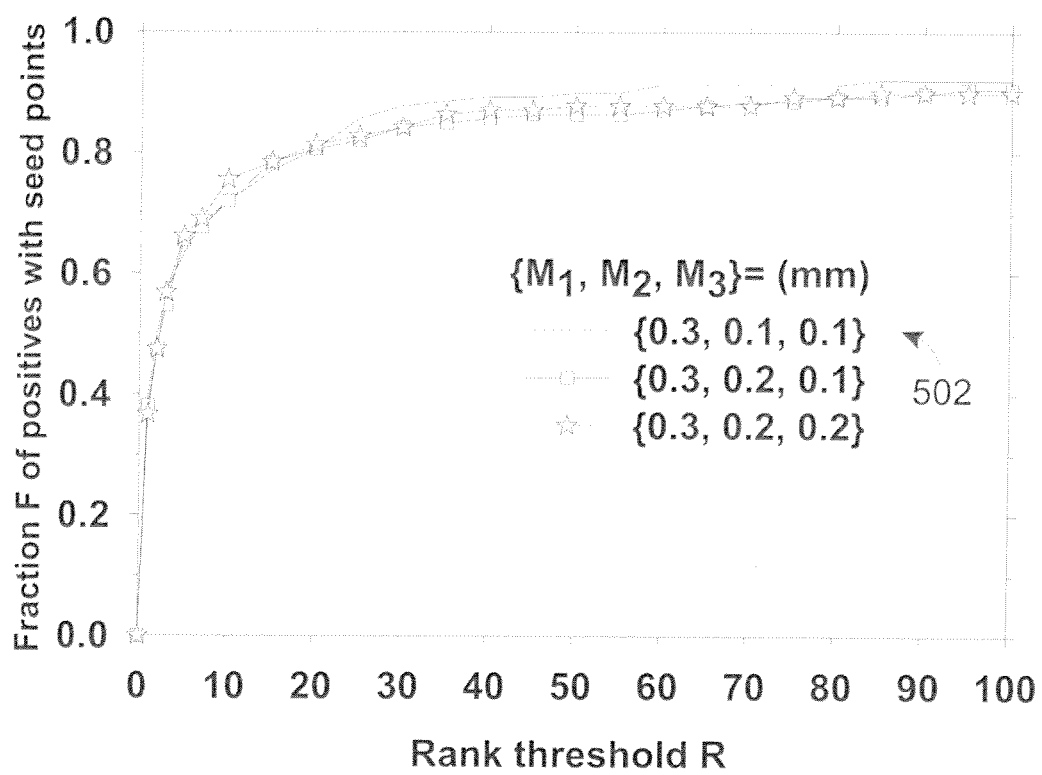
FIGS. 5a, 5b, and 5c are illustrations of graphs depicting examples of the effect of changes to the size of the inner filter kernels ($M_2$ and $M_3$) prescreening performance in a method and system to detect microcalcification clusters in DBT volumes.
Figure 5B:
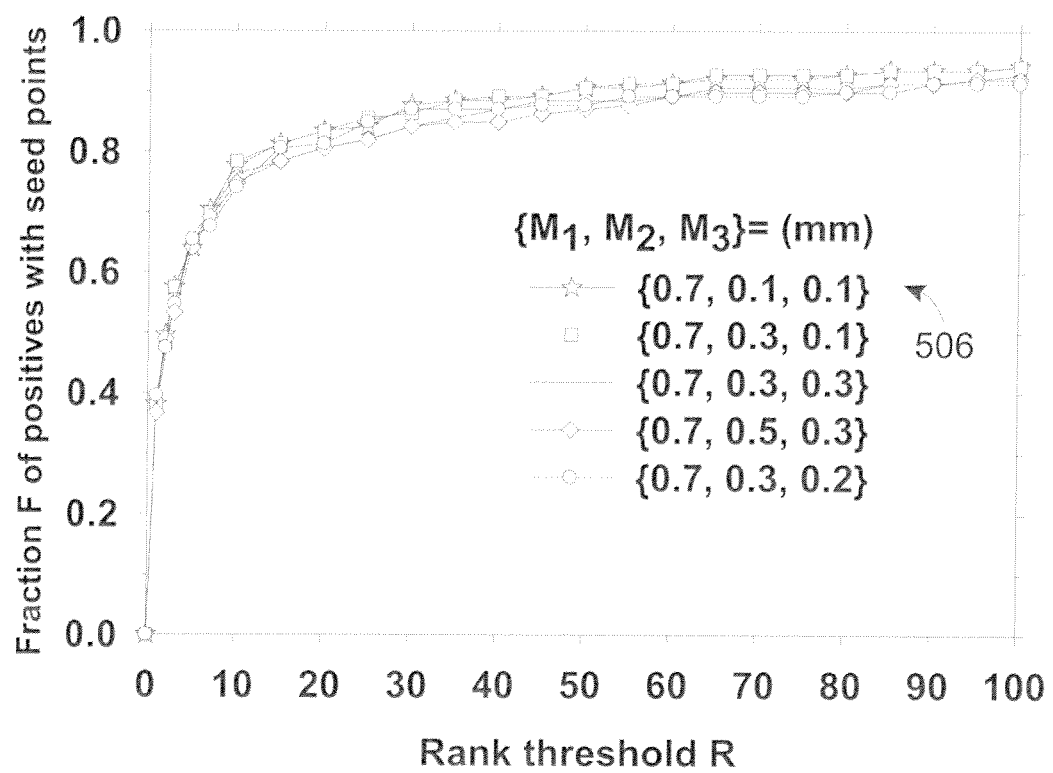
Figure 5C:
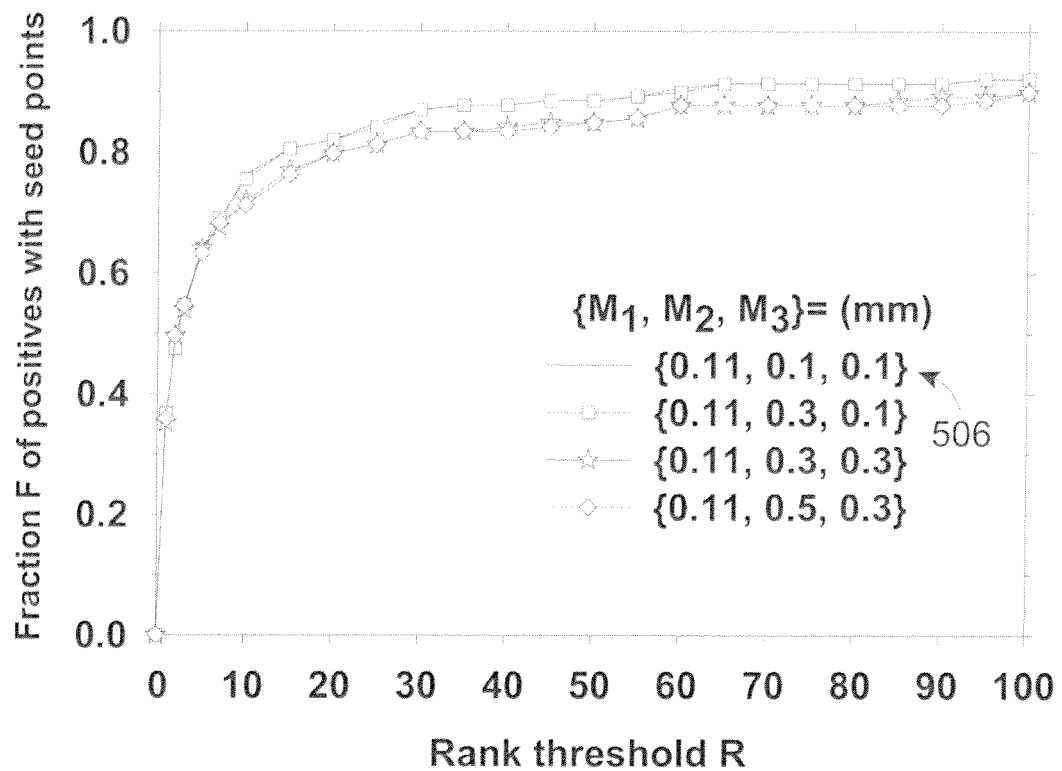

FIGS. 5a, 5b, and 5c illustrate the effect of varying $M_2$ and $M_3$ for $M_1$=0.3, 0.7, and 0.11 mm, respectively. In some embodiments, setting $M_1$=0.7 mm, $M_2$=0.1 mm, and $M_3$=0.1 mm for the SNR enhancement, at an operating point of 100 objects per DBT volume, results in 94% of biopsied calcification clusters actually containing a seed point (as shown in FIG. 5b).

C. Effect of Enhancement Modulated Calcification Response

Figure 6:
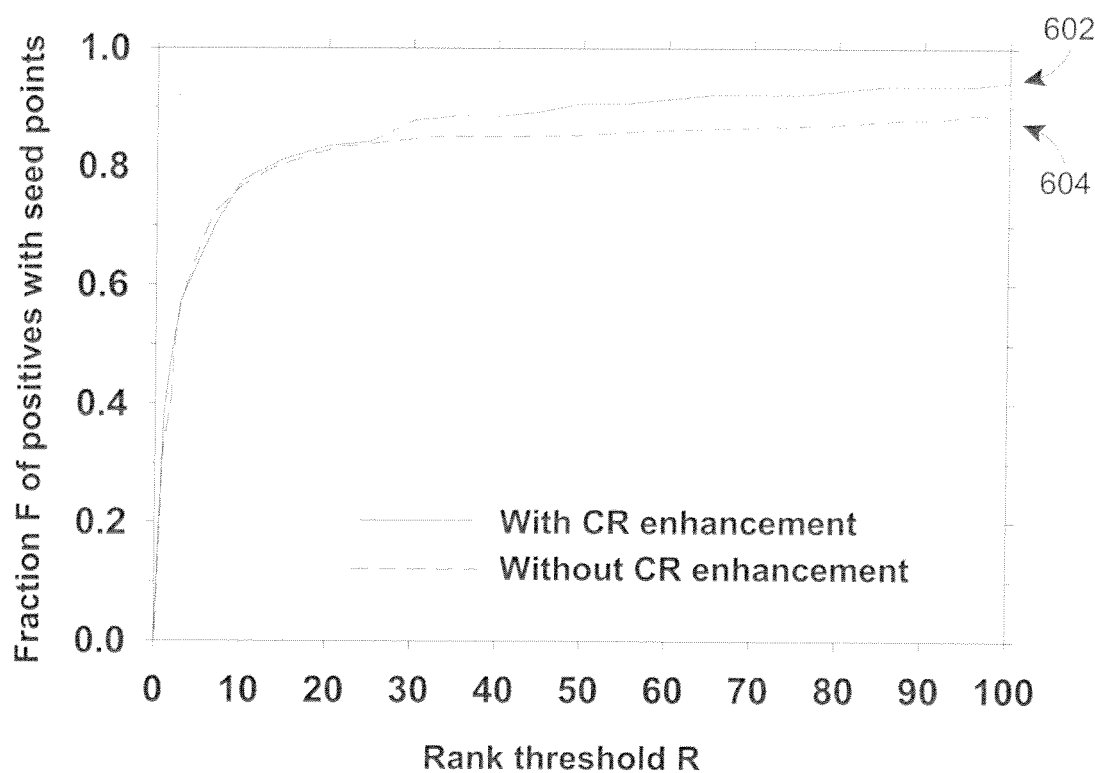
FIG. 6 is an illustration of a graph depicting an example of rank-sensitivity plots for the prescreening performance in a method and system to detect microcalcification clusters in DBT volumes with and without the multi-scale calcification response (CR) enhancement.

Modulating the result of the multi-scale calcification response function, method or module 116 (e.g., the calcification response 122) with the SNR-enhanced image 220 (FIG. 2b) may also be evaluated by comparing the prescreening rank-sensitivity plot with the calcification response function in place ($\{\sigma\}=\{0.20$ mm, 0.25 mm, 0.35 mm$\}$) so that the output of multi-scale calcification response 122 (see FIG. 1) may be replaced by a spatially-constant value over the DBT volume. In this evaluation, only SNR-enhancement was applied during pre-screening when the multi-scale calcification response enhancement was removed. The parameters of the SNR enhancement filter may be $M_1$=0.7 mm, $M_2$=0.1 mm, and $M_3$=0.1 mm, as discussed above. FIG. 6 shows a comparison of the two pre-screening approaches such that the prescreening performance with multi-scale calcification response (CR) enhancement 602 is higher than that without CR enhancement 604.

D. Effect of Clustering and False-Positive Reduction

Figure 7:
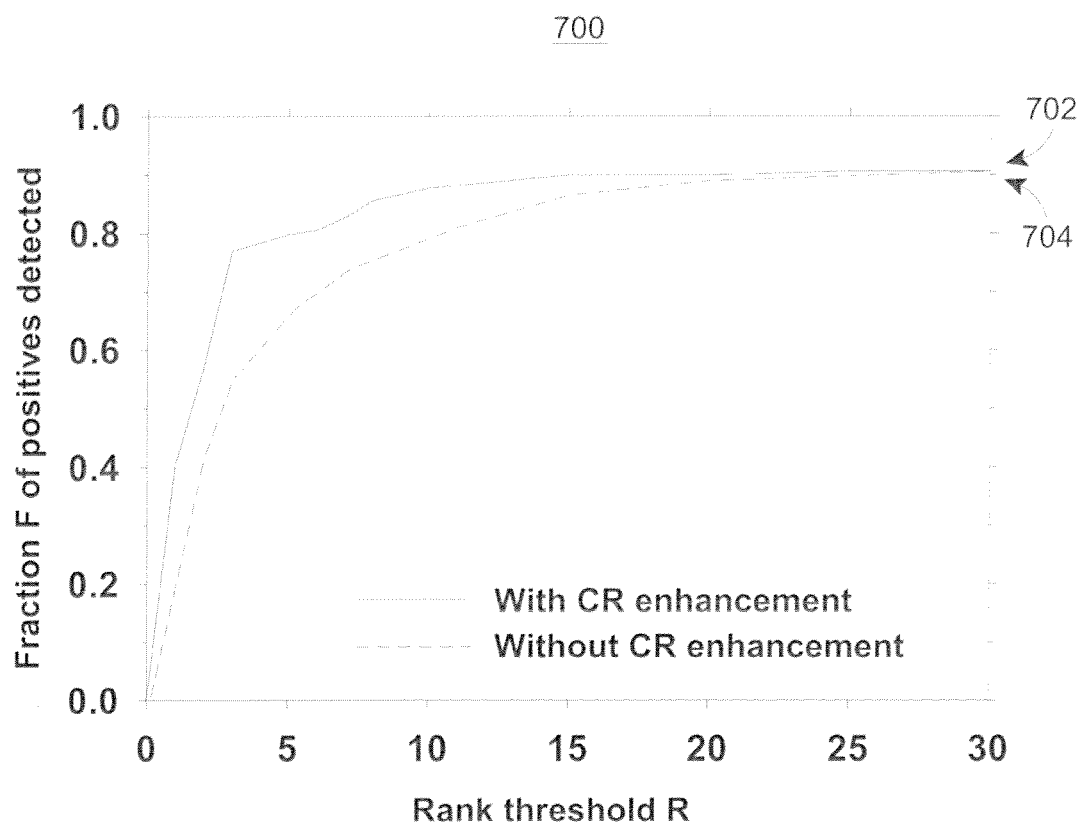
FIG. 7 is an illustration of a graph depicting an example of rank-sensitivity plots for the clustering performance in a method and system to detect microcalcification clusters in DBT volumes with and without the multi-scale calcification response (CR) enhancement.

FIG. 7 illustrates a comparison of the system performance after the clustering stage with and without the multi-scale calcification response enhancement described above. The comparison 700 plots rank-sensitivity using the SNR of the object with the highest SNR value within a cluster as the decision variable. As shown in FIG. 7, at an operating point of 15 objects per DBT volume, 90% of biopsied calcification clusters may be correctly identified.

Figure 8A:
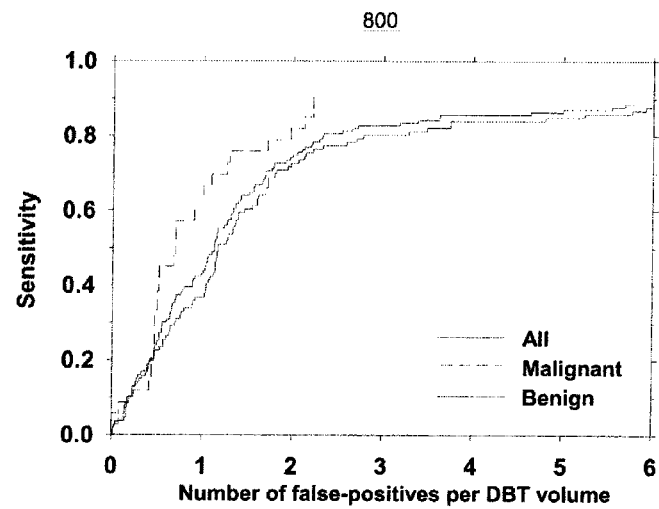
FIGS. 8a and 8b are illustrations of a graph depicting the view-based and case-based performance of the system and method for detection of microcalcification clusters in DBT volumes.
Figure 8B:
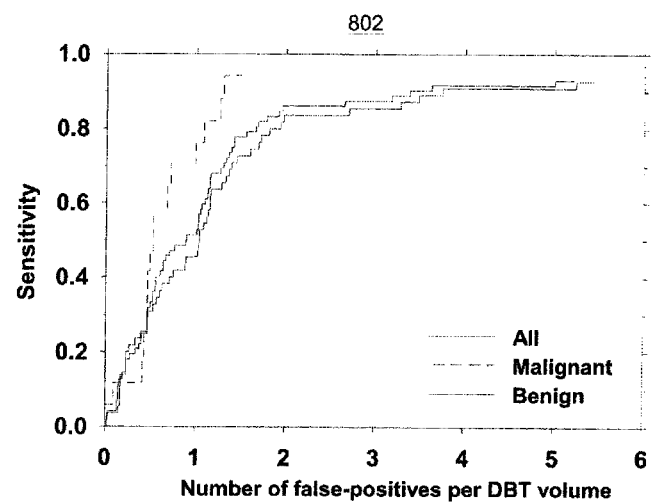

FIGS. 8a and 8b illustrate free response receiver operating characteristics (FROC) curves for the detection system, after using the false-positive reduction techniques described herein, for view-based 800 and case-based 802 scoring, respectively. In view-based scoring 800, the same cluster seen in the CC and MLO views was counted independently. In case-based scoring 802, a cluster was considered to be detected if its score exceeded the decision threshold in either one or both of CC and MLO views. The performance of the CAD system 100 was evaluated in a data set as an example. Of course the specific performance values will depend on the data set used. Using view-based scoring 800, the average number of FPs over the entire data set was 3.62 and 2.33 per DBT volume at 85% and 80% sensitivity, respectively. The false positive rates at these sensitivity levels for both scoring methods for the entire data set, the malignant subset, and the benign subset are shown in Table 1.

TABLE 1

| Clusters | 80% sensitivity (view-based) | 85% sensitivity (view-based) | 80% sensitivity (case-based) | 85% sensitivity (case-based) |
|---|---|---|---|---|
| All | 2.33 | 3.62 | 1.66 | 1.96 |
| Malignant | 1.97 | 2.20 | 1.09 | 1.26 |
| Benign | 2.77 | 5.23 | 1.93 | 3.48 |

V. Discussion

As illustrated by FIGS. 3-8 and Table 1, 3D enhancement-modulated calcification response may be used to detect microcalcification clusters in reconstructed DBT volumes. As described herein, two calcification enhancement processes are used in some embodiments: (1) enhancement of calcification response based on Hessian analysis, and (2) SNR enhancement based on difference of filters. The SNR enhancement technique may be effective in highlighting small, high-contrast objects, as demonstrated by the example image in FIG. 2b. However, the SNR enhancement technique may also enhance line-type structures, resulting in false positive detections in the prescreening stage. These false positive detections may propagate to other stages of the detection system. FIGS. 6 and 7 indicate that the combination of the two enhancement processes resulted in an improved performance compared to SNR enhancement alone.

The calcification response derived from multi-scale filters with the smallest widths 302 ($\{\sigma\}=\{0.15$ mm, 0.20 mm, 0.30 mm$\}$) may have a lower rank-sensitivity plot than the other sets, as shown in FIG. 3. This lower rank-sensitivity plot may indicate that larger microcalcifications were more important for higher detection performance in this data set. For SNR enhancement, the size of the outer box used for background estimation, $M_1$, may not have a major effect 402 on the prescreening performance, as shown in FIG. 4, when it was 0.5 mm or larger. Because most microcalcifications of interest are smaller than 0.5 mm, the result illustrated by FIG. 4 may be consistent with the expectation that the background should be estimated in a small region surrounding the microcalcification without including the calcification itself. The prescreening performance may be slightly degraded when the inner box sizes were increased from $(M_2, M_3)$=(0.1 mm, 0.1 mm), 502, 504, 506, as shown in FIGS. 6a, 6b, and 6c. The final choice of $(M_1, M_2, M_3)$=(0.7 mm, 0.1 mm, 0.1 mm) 504 may show that the reconstructed DBT slices were relatively smooth so that no additional smoothing was needed to achieve the best SNR. Using the techniques described herein, a case-based sensitivity of approximately 80% or higher may be obtained at about 1.1 false-positive per DBT volume, while the false positive rate may be about 1.9 for benign clusters at the same sensitivity. The performance may improve or decrease by adjusting the parameters at the various stages of the CAD system 100.

The techniques described herein may be used with DBT volumes that are reconstructed using various methods. While the above methods indicate using the SART method for reconstruction, other reconstruction techniques such as filtered-backprojection or maximum-likelihood reconstruction methods may be used. These other methods may also have different noise and signal properties, which may require an adjustment of parameters.

In some embodiments, spherically symmetric microcalcifications may be detected. Other embodiments, a variety of microcalcifications shapes, including oblong and irregular may be detected. In addition, inter-plane artifacts from the reconstruction algorithm may distort the shape of the microcalcifications in the depth direction. As such, the design of the parameters for the methods described herein may take into consideration the anisotropic properties of the signal and the noise. For example, accurate modeling of the electronic, quantum, and structured noise components, the microcalcification signal, and the artifacts introduced by the limited-angle reconstruction may improve the detection performance.

The CAD 100 system described herein detects microcalcification clusters in reconstructed DBT volumes by enhancing microcalcifications using an 3D enhancement-modulated calcification response (EMCR) function. The CAD system 100 for 3D detection in the reconstructed volume may be combined with 2D detection on PVs to improve the overall detection performance of microcalcification clusters in DBT, The CAD system 100 may be useful as a second reader to assist radiologists in detection of clustered microcalcifications in DBT.

VI. Combined 3D and 2D Method for CAD

Figure 9A:
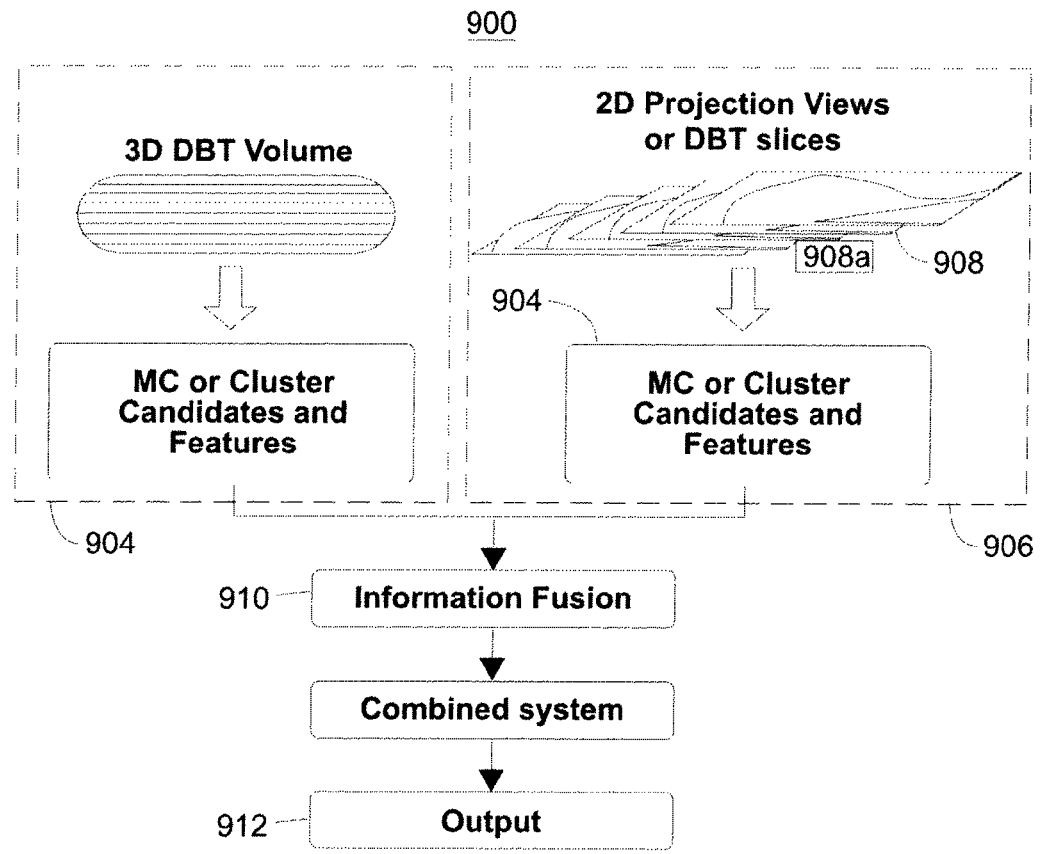
FIG. 9a is an exemplary flow chart of several blocks in a microcalcification detection system for DBT.

FIG. 9a illustrates one embodiment of a combined 3-dimensional (3D) and 2-dimensional (2D) method 900 for computerized detection of microcalcification clusters in individual DBT slices (or slabs) and that information may be merged with the information in 3D. The combined method 900 may include a 3D method 904 as described above in relation to FIG. 1, and a 2D method 906 as described below. A DBT slice is similar in appearance to a full field digital mammogram (FFDM) except for the reduced tissue overlap so that each slice can be processed as if it is a 2D mammogram. The DBT slabs can be considered thicker DBT slices for image processing purposes. Image processing before the clustering stage may be performed and optimized based on the characteristics of the 2D images 908. By using the 2D images 908, the image analysis methods do not have to handle the anisotropic resolution of DBT directly. After the 2D processing 906, an individual object that may appear in adjacent slices will be identified by its spatial location and connectivity. Because MCs in a cluster 204 (FIG. 2) may spread over several slices and make the cluster more difficult to detect, clustering and cluster feature analysis may be performed in 3D across the slices using the same methods and modules described in relation to FIG. 1.

The DBT slices generated by any of the MC-enhancement methods described in relation to FIG. 1 may be used as input to this combined 2D/3D approach. After pre-screening 104 and segmentation 106, 2D features found to be useful for mammograms may be extracted for FP reduction 108.

A. 2D Approach

A 2D approach 906 may generally proceed with an input of 2D projection view (PV) images before reconstruction, or reconstructed 2D DBT slice images 908. With 2D projection view images or DBT slice/slab images as input, prescreening of MC candidates on the images may be performed with any known methods similar to those for full field digital mammograms (FFDMs). In other embodiments, a 2D candidate analysis stage 906 may include a multi-channel enhancement (MCE) response method to enhance prescreened objects. In some embodiments, the 2D candidate analysis stage 906 may also include a weighted combination of basis functions trained to represent the signals.

B. Multi-Channel Enhancement (MCE) Method

The MCE method of the 2D candidate analysis stage 906 enhances microcalcifications on two-dimensional (2D) projection views (or 2D DBT slices/slabs), and differentiates true and false microcalcifications. The MCE method may generally consider a 2D image 908 as a 2D function which contains a set of characteristics 908a. These characteristics 908a can be represented by a set of 2D orthogonal basis functions. If the set of orthogonal basis functions is properly chosen, each image 908 can be characterized by a small number (N) of basis functions. Each basis function is referred to as a channel, and the set of basis functions is a multi-channel set. The candidate analysis stage 906 then determines the appropriate set of multi-channels $\{b_1, \ldots b_N\}$ that can most effectively describe the characteristics of the type of images of interest and the set of channel response $\{g_1, \ldots, g_N\}$ for each image 908 given the multi-channel set.

To detect microcalcifications on a 2D projection view (or DBT slice/slab), a number of microcalcification candidates in the PV are first identified by a prescreening method. A local region of interest (ROI) of p×p pixels centered at each microcalcification candidate is extracted, which is a 2D image of p×p pixels. Some of the ROIs contain true microcalcifications and some are false positives. Each ROI can then be characterized by the a set of channel response $\{g_1, \ldots, g_N\}$i given a multi-channel set, as described above. The set of channel response $g=\{g_1, \ldots, g_N\}$i can be considered a vector representing the ROI image.

With this representation, the task of differentiating the true and false microcalcification candidates can be formulated as a linear classification model to classify a given vector g into one of the two classes:

$$D(g)=(\overline{m_2}-\overline{m_1})^T\Sigma^{-1}g \quad \text{(Equation 11)}$$

where $\overline{m_k}$ the mean vector for class k, k=1,2 and $\Sigma$ is an N×N covariance matrix.

The multi-channel set and the number N may be selected by training with sample ROI images of the two classes to optimize the channel response and the classification performance. $\Sigma$ is the covariance matrix of the class distributions estimated from the training samples. The multi-channel set can be chosen as, but is not limited to, the Laguerre polynomials multiplied by the Gaussian functions. The vectors (g) representing the ROIs will have different values for each different set of multi-channels.

Once the classification model in Equation 11 is trained, the model can be incorporated into the CAD system for enhancement and characterization of MCs in 2D projection views (or DBT slices/slabs) 906. We refer to the output D(g) of the model as the multi-channel enhancement (MCE) response. The MCE response represents the strength of the microcalcification characteristics in the ROI image.

For DBT slices/slabs 908, the MCE response can be used as a decision variable to differentiate true and false MCs, or used in combination with other MC features to generate the cluster likelihood score (CLS) and the level of suspicion (LOS) and the overall cluster significance rating (CSR), as described below.

For PV images, the MCE-responses for the individual MC candidates on the PVs may be ray-traced (i.e., back-projected) back to the 3D DBT volume (and thus the DBT slices) by using the imaging geometry of DBT. True MCs from the PVs corresponding to the same MC in the breast would converge and the MCE-response will be amplified whereas the false positives (FPs) rarely will intersect and, thus, the FPs would be muted.

The output back-projected MCE-responses 904 may then be analyzed. If the MCE enhancement is performed on the 2D projection views, they will be backprojected (or ray-traced) to the 3D breast volume to localize the potential calcifications in 3D. The backprojected MCE response may be treated as a microcalcification-enhanced 3D image 110 (FIG. 1) and analyzed using feature extraction techniques such as adaptive thresholding, extraction of local maxima, and clustering. In addition, the backprojected MCE response may be used in conjunction with the 3D approach 904 as described herein.

In either the 3D approach of FIG. 1 or the combined 2D/3D approach of FIG. 9a, the output of the CAD system will include the locations of the suspicious clusters and a cluster significance rating (CSR) for each cluster in an information fusion module 910. The CSR is defined as the cluster likelihood score (CLS) weighted with an additional rating that represents the level of suspicion (LOS) of being a malignant cluster that needs to be worked up. The idea of the CSR is important because, at the output of a CAD system, the cluster candidates may include subtle but significant clusters, and obvious but not very suspicious clusters, and false positives. If the final stage classifier is trained only to differentiate true and false clusters, subtle significant clusters may fall below the decision threshold. The LOS weighting increases the chance that a subtle but significant cluster to be prompted by the CAD system.

Figure 9B:
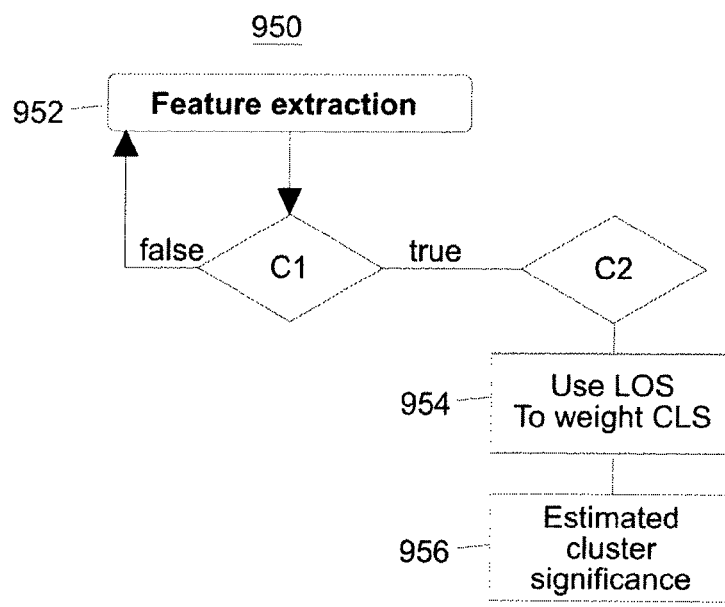
FIG. 9b is an exemplary flow chart of several blocks method for estimating a cluster significance rating.

With reference to FIG. 9b, the CSR may be estimated for each cluster using a method 950 including several steps or function blocks applied to an output of the 3D approach (FIG. 1), the 2D approach 906, or the combined 3D/2D approach 900 (FIG. 9a). At block 952, a number of features may be extracted from the 3D DBT volume 112 (FIG. 1), 2D DBT slices, and/or the 2D projection view images 908 (FIG. 9a). The extracted features may include, but are not limited to: (1) descriptors of the morphology and spatial distribution of the individual calcifications (e.g., the size, the contrast-to-noise ratio, mean density, degree of elongation, and degree of irregularity), (2) descriptors of cluster features (e.g., the number of MCs in the cluster, the size and shape of the convex hull enclosing the cluster, the variations of the individual MC features within the cluster, expressed as the standard deviation, the coefficient of variation, and the range, spatial features such as the variation of the distances between cluster members, vascular calcifications or not), (3) descriptors of breast tissue texture containing the MC cluster, (4) the enhancement-modulated calcification response (EMCR), (5) the multi-channel enhancement (MCE) response, (6) the convolution neural network (CNN) response, and (7) features to differentiate vascular calcifications from clinically significant clustered MCs.

After feature extraction, a classifier may be trained to classify the detected clusters as true and false, and, if a cluster is called true, estimate its LOS. The LOS may then be used to weight the CLS from the first-stage classification, resulting in a cluster significance rating (CSR) to increase sensitivity of detecting clinically significant clusters. A first classifier (C1) that has been trained to classify the clusters as true or false will determine the cluster's CLS. If the cluster is considered a true cluster by its CLS, a second classifier (C2) that has been trained to classify a cluster as malignant or benign will determine its LOS. At block 954, the LOS will then be used to weight the CLS from the first-stage classification, resulting in an estimated cluster significance rating (CSR) 956 to increase sensitivity of detecting clinically significant clusters. If C1 classifies the cluster as false, then the method 950 starts over and analyzes the next cluster. The combined 2D/3D approach 900 may generally increase the visibility of MCs in PVs and DBTs. The MCE response described above may enhance the MCs in a 2D approach 906 and provide an additional feature for other analyses (e.g., the estimation of a CSR, above). Further, the backprojected MCE response described above may be used in place of the MC-enhanced image 110 (FIG. 1) described in relation to the 3D approach of FIG. 1.

Figure 10:
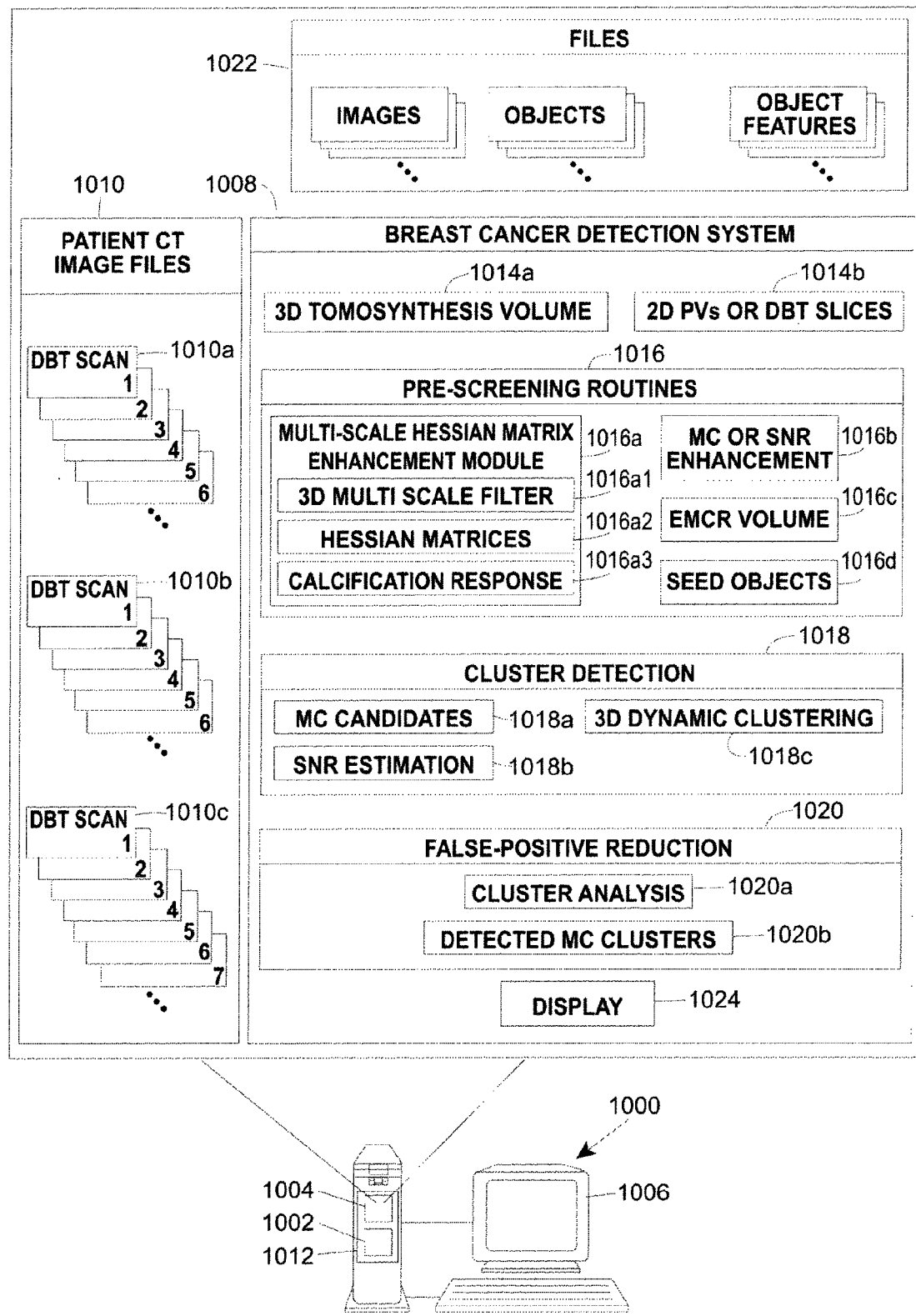
FIG. 10 is a block diagram of a computer aided detection system that can be used to detect clustered microcalcifications in Digital Breast Tomosynthesis (DBT)

Referring to FIG. 10, the computer aided detection (CAD) method and system of FIGS. 1 and 9 may be implemented using several modules as described herein to detect and diagnose breast cancers. In one embodiment, a computer 1012 having a processor 1002 and a memory 1004 therein and having a display screen 1006 associated therewith. As illustrated in an expanded view of the memory 1004, a breast cancer detection and diagnostic system 1008 in the form of, for example, a program written in computer executable instructions or code, is stored in the memory 1004 and is adapted to be executed on the processor 1002 to perform processing on one or more sets of DBT images 1010, which may also be stored in the computer memory 1004. The DBT images 1010 may include DBT images for any number of patients and may be entered into or delivered to the system 900 using any desired importation technique. Generally speaking, any number of sets of images 1010*a*, 1010*b*, 1010*c*, etc. (called image files) can be stored in the memory 1004 wherein each of the image files 1010*a*, 1010*b*, 1010*c*, etc. includes numerous DBT scan images associated with a particular DBT scan of a particular patient. Thus, different ones of the images files 1010*a*, 1010*b*, 1010*c*, etc. may be stored for different patients or for the same patient at different times. As noted above, each of the image files 1010*a*, 1010*b*, 1010*c*, etc. includes a plurality of images therein corresponding to the different slices of information collected by a DBT imaging system during a particular DBT scan of a patient. The actual number of stored scan images in any of the image files 1010*a*, 1010*b*, 1010*c*, etc. will vary depending on the size of the patient, the scanning thickness, the type of DBT system used to produce the scanned images in the image file, etc. While the image files 1010 are illustrated as stored in the computer memory 1004, they may be stored in any other memory and be accessible to the computer 1012 via any desired communication network, such as a dedicated or shared bus, a local area network (LAN), wide area network (WAN), the internet, etc.

As also illustrated in FIG. 10, the breast cancer detection and diagnostic system 1008 includes a number of modules, components, or routines which may perform different steps or functionality in the process of analyzing one or more of the image files 1010 to detect breast cancers. As explained in more detail above, the breast cancer detection and diagnostic system 1008 may include 3D tomo volume analysis routines 1014*a*, 2D PV and DBT slice/slab routines 1014*b*, as well as Pre-screening routines 1016, cluster detection routines 1018, and false-positive reduction routines 1020. The prescreening routines 1016 may include a multi-scale Hessian matrix enhancement module 1016*a*, MC or SNR Enhancement Routines 1016*b* (or the multi-channel enhancement (MCE) methods described herein), EMCR volume routines 1016*c*, and seed object routines 1016*d*. The multi-scale Hessian matrix enhancement module 1016*a* may include 3D multi-scale filter routines 1016*a*1, Hessian matrix routines 1016*a*2, and calcification response routines 1016*a*3. The cluster detection routines 1018 may include MC candidates routines 1018*a*, SNR estimation routines 1018*b*, and 3D dynamic clustering routines 1018*c*. The False Positive reduction routines 1020 may include cluster feature analysis routines 1020*a*, and detected MC clusters routines 1020*b*. Of course other modules, routines, and devices may be included within the system 1008 as needed.

Still further, the CAD system 1000 may include a set of files 1022 that store information developed by the different routines 1014-1024 of the system 1000. These files 1022 may include temporary image files that are developed from one or more of the DBT images within an image file 1010 and object files that identify or specify objects within the DBT images. The files 1022 may also include one or more object files specifying the location and boundaries of objects that may be considered as cluster candidates, and object feature files specifying one or more features of each of these cluster candidates as determined by the detected MC clusters routines 1020*b*. Of course, other types of data may be stored in the different files 1022 for use by the system 1000 to detect breast cancers from the DBT images of one or more of the image files 1010.

Still further, the breast cancer detection and diagnostic system 1008 may include a display program or routine 1024 that provides one or more displays to a user, such as a radiologist, via, for example, the screen 1006. Of course, the display routine 1024 could provide a display of any desired information to a user via any other output device, such as a printer, via a personal data assistant (PDA) using wireless technology, etc.

During operation, the breast cancer detection and diagnostic system 1008 operates on a specified one or ones of the image files 1010*a*, 1010*b*, 1010*c*, etc. to detect microcalcifications associated with the selected image file. After performing the detection function, which is described in more detail above, the system 1000 may provide a display to a user, such as a radiologist, via the screen 1006 or any other output mechanism, connected to or associated with the computer 1000 indicating the results of the breast cancer detection process. Of course, the CAD system 1000 may use any desired type of computer hardware and software, using any desired input and output devices to obtain DBT images and display information to a user and may take on any desired form other than that specifically illustrated in FIG. 10.

Figure 11:
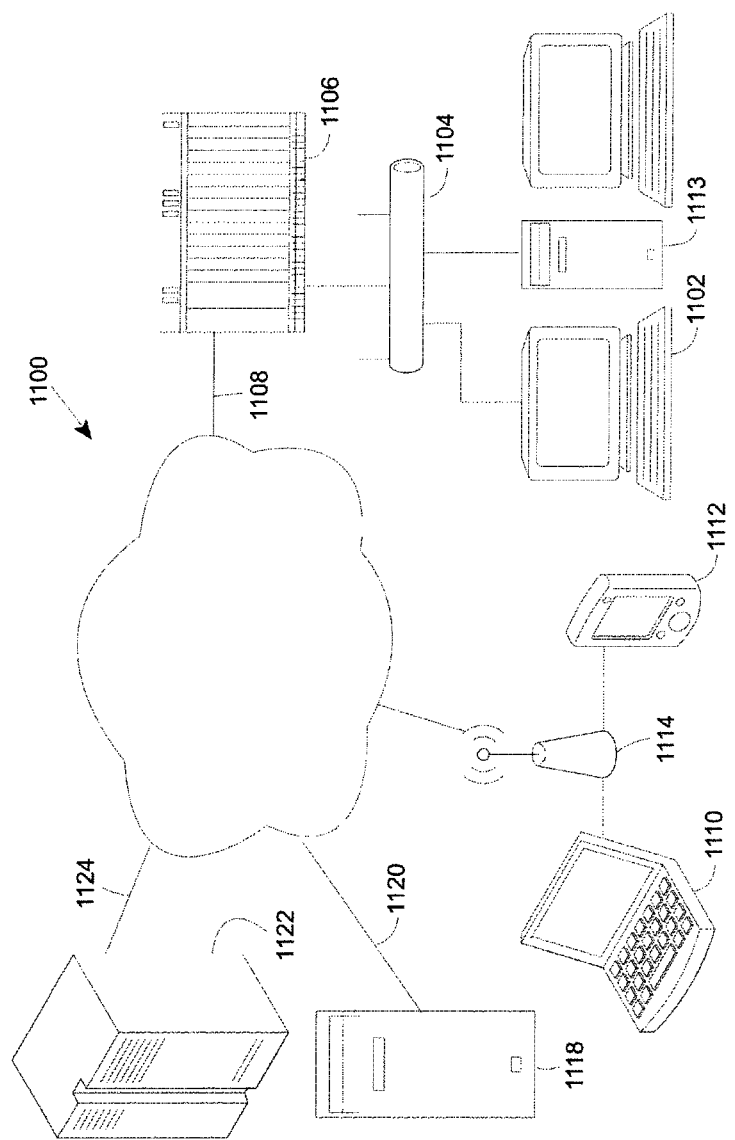
FIG. 11 illustrates an example computer network.
Figure 12:
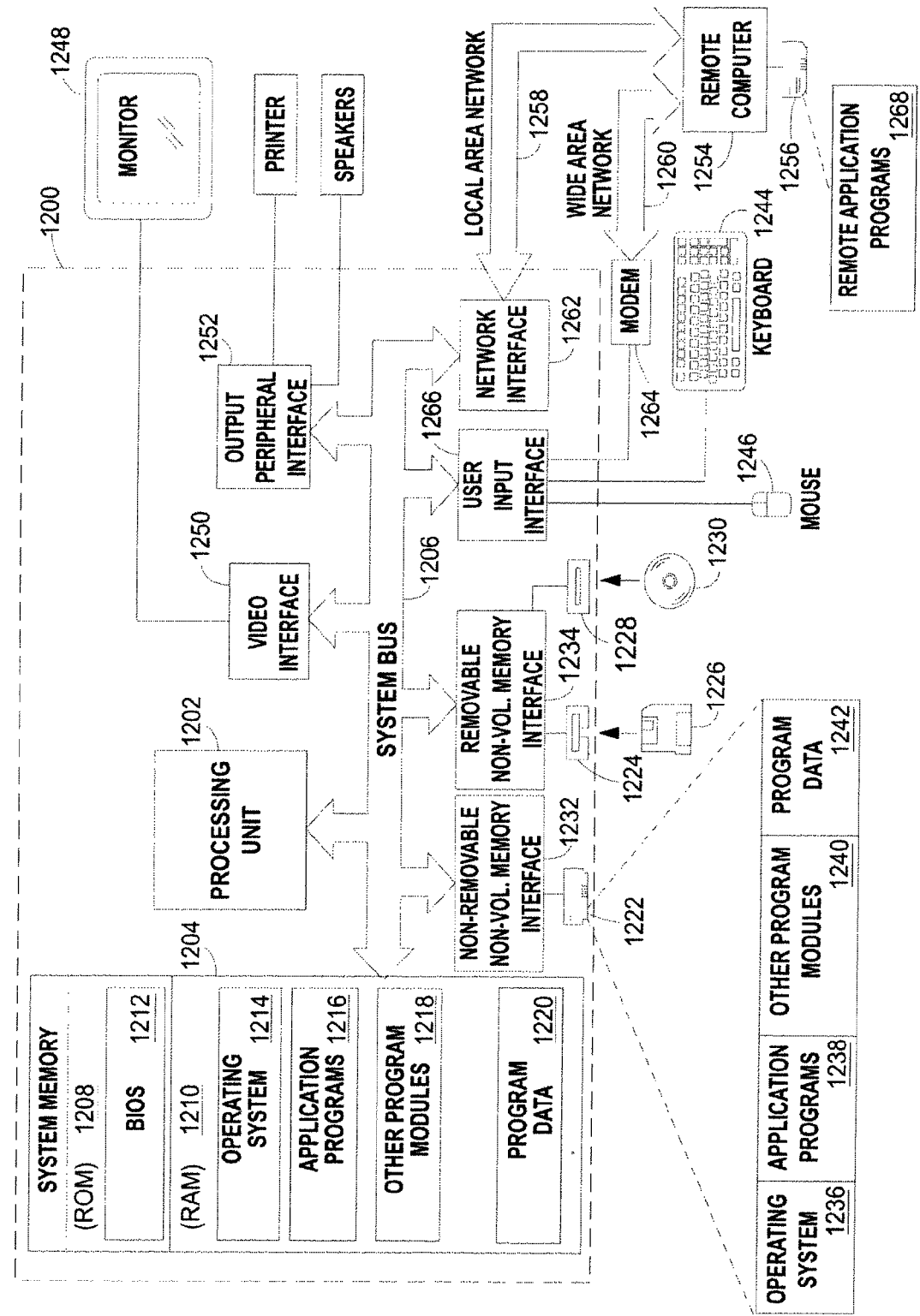
FIG. 12 illustrates an example computer that may be connected to the network of FIG. 10.
Figure 13:
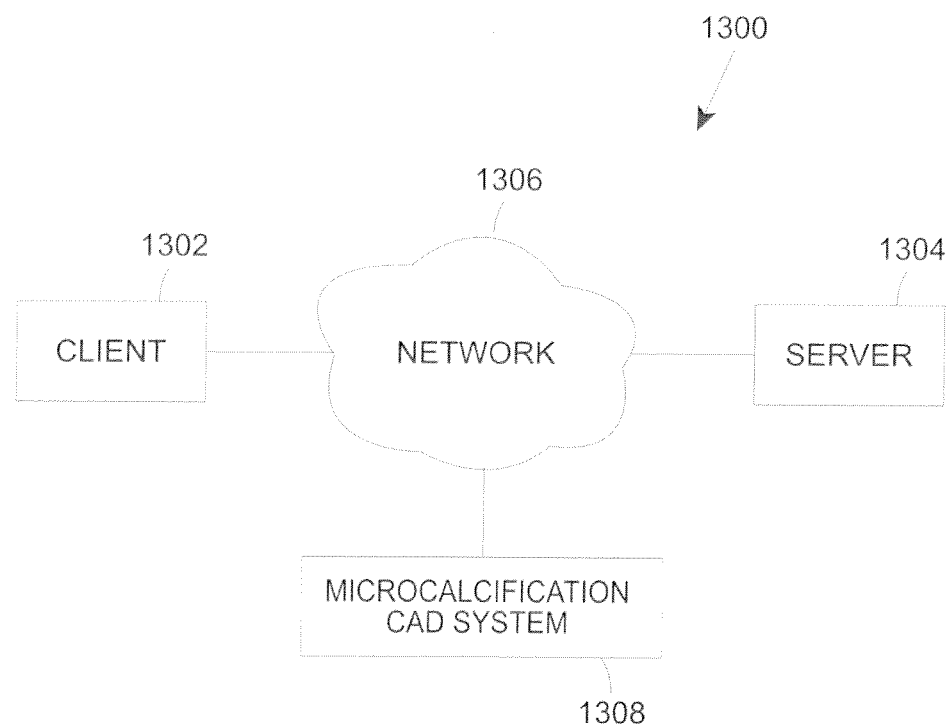
FIG. 13 illustrates an example computer aided microcalcification detection system.

The CAD system 1000 may also include other interconnected and integrated components used in a computerized microcalcification detection system. FIGS. 11-13 provide additional structural bases for the network and computational platforms related to such a system.

FIG. 11 illustrates a network 1100. The network 1100 may be the Internet, a virtual private network (VPN), or any other network that allows one or more computers, communication devices, databases, etc., to be communicatively connected to each other. The network 1100 may be connected to a personal computer 1113, and a computer terminal 1102 via an Ethernet 1104 and a router 1106, and a landline 1108. The Ethernet 1104 may be a subnet of a larger Internet Protocol network. Other networked resources, such as projectors or printers (not depicted), may also be supported via the Ethernet 1104 or another data network. On the other hand, the network 1100 may be wirelessly connected to a laptop computer 1110 and a personal data assistant 1112 via a wireless communication station 1114 and a wireless link 1116. Similarly, a server 1118 may be connected to the network 1100 using a communication link 1120 and a mainframe 1122 may be connected to the network 1100 using another communication link 1124. The network 1100 may be useful for supporting peer-to-peer network traffic.

FIG. 12 illustrates a computing device in the form of a computer 1200. Components of the computer 1200 may include, but are not limited to a processing unit 1202, a system memory 1204, and a system bus 1206 that couples various system components including the system memory to the processing unit 1202. The system bus 1206 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 1200 typically includes a variety of computer readable media. Computer readable media can be any available media that can be accessed by computer 1200 and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 1200. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer readable media.

The system memory 1204 includes computer storage media in the form of volatile and/or nonvolatile memory such as read only memory (ROM) 1208 and random access memory (RAM) 1210. A basic input/output system 1212 (BIOS), containing the basic routines that help to transfer information between elements within computer 1200, such as during start-up, is typically stored in ROM 1208. RAM 1210 typically contains data and/or program modules that are immediately accessible to and/or presently being operated on by processing unit 1202. By way of example, and not limitation, FIG. 12 illustrates operating system 1214, application programs 1216, other program modules 1218, and program data 1220.

The computer 1200 may also include other removable/non-removable, volatile/nonvolatile computer storage media. By way of example only, FIG. 11 illustrates a hard disk drive 1222 that reads from or writes to non-removable, nonvolatile magnetic media, a magnetic disk drive 1224 that reads from or writes to a removable, nonvolatile magnetic disk 1226, and an optical disk drive 1228 that reads from or writes to a removable, nonvolatile optical disk 1230 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1222 is typically connected to the system bus 1206 through a non-removable memory interface such as interface 1232, and magnetic disk drive 1224 and optical disk drive 1228 are typically connected to the system bus 1206 by a removable memory interface, such as interface 1234.

The drives and their associated computer storage media discussed above and illustrated in FIG. 12, provide storage of computer readable instructions, data structures, program modules and other data for the computer 1200. In FIG. 12, for example, hard disk drive 1222 is illustrated as storing operating system 1236, application programs 1238, other program modules 1240, and program data 1242. Note that these components can either be the same as or different from operating system 1236, application programs 1238, other program modules 1240, and program data 1242. Operating system 1236, application programs 1238, other program modules 1240, and program data 1242 are given different numbers here to illustrate that, at a minimum, they are different copies. A user may enter commands and information into the computer 1200 through input devices such as a keyboard 1244 and cursor control device 1246, commonly referred to as a mouse, trackball or touch pad. A monitor 1248 or other type of display device is also connected to the system bus 1206 via an interface, such as a graphics controller 1250. In addition to the monitor, computers may also include other peripheral output devices which may be connected through an output peripheral interface 1252.

The computer 1200 may operate in a networked environment using logical connections to one or more remote computers, such as a remote computer 1254. The remote computer 1254 may be a personal computer, a server, a router, a network PC, a peer device or other common network node, and typically includes many or all of the elements described above relative to the computer 1200, although only a memory storage device 1256 has been illustrated in FIG. 12. The logical connections depicted in FIG. 12 include a local area network (LAN) 1258 and a wide area network (WAN) 1260, but may also include other networks. Such networking environments are commonplace in offices, enterprise-wide computer networks, intranets and the Internet.

When used in a LAN networking environment, the computer 1200 is connected to the LAN 1258 through a network interface or adapter 1262. When used in a WAN networking environment, the computer 1200 typically includes a modem 1264 or other means for establishing communications over the WAN 1260, such as the Internet. The modem 1264, which may be internal or external, may be connected to the system bus 1206 via the input interface 1266, or other appropriate mechanism. In a networked environment, program modules depicted relative to the computer 1200, or portions thereof, may be stored in the remote memory storage device. By way of example, and not limitation, FIG. 12 illustrates remote application programs 1268 as residing on memory device 1256.

The communications connections 1262, 1264 allow the device to communicate with other devices. The communications connections 1262, 1264 are an example of communication media. The communication media typically embodies tangible computer readable instructions, data structures, program modules or other data transformed to a modulated data signal such as a carrier wave or other transport mechanism and includes any information delivery media. A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Computer readable media may include both storage media and communication media.

FIG. 13 illustrates an example electronic microcalcification detection system 1300. The microcalcification detection system 1300 may include (or be modified to include) one or more client computing devices 1302, one or more server computing devices 1304 and one or more computing devices associated with a CAD system 1308. Portions of a microcalcification detection application may be implemented on one or more of the client computing devices 1302, one or more of the server computing devices 1304 or one or more computing devices associated with the CAD system 1308, or a combination thereof. The detection application may also implement analysis routines, such as those described in reference to FIG. 1. Alternatively, the analysis routines may be implemented elsewhere in the detection system 1300.

In some embodiments, one computing device may be configured to receive, from another computing device, data corresponding to DBT images. In response, the second computing device may perform various analyses, as described above in more detail.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, functions, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "code," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "some embodiments," "one embodiment" or "an embodiment" means that a particular element, feature, structure, or characteristic described in connection with the embodiment is included in at least one embodiment. The appearances of the phrase "in one embodiment" or "in some embodiments" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for identifying a path through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A computer-implemented method for detecting a microcalcification cluster in reconstructed volumes of a three-dimensional digital breast tomosynthesis image, comprising:
   receiving, at a computing device, a three-dimensional digital breast tomosynthesis image;
   reconstructing, at the computing device, the three-dimensional digital breast tomosynthesis image to create a reconstructed three-dimensional digital breast tomosynthesis image;
   enhancing, at the computing device, a microcalcification candidate in each slice of the reconstructed three-dimensional digital breast tomosynthesis image to obtain an enhanced three-dimensional digital breast tomosynthesis image by simultaneously:
   1) determining a multi-scale calcification response for each voxel (x,y,z) of the microcalcification candidate, and
   2) one of:
      a) enhancing a signal-to-noise ratio of a microcalcification in the reconstructed three-dimensional digital breast tomosynthesis image, or
      b) enhancing a signal intensity of the microcalcification in the reconstructed three-dimensional digital breast tomosynthesis image;
   wherein the multi-scale calcification response includes:
      a) filtering the reconstructed three-dimensional digital breast tomosynthesis image with a plurality of smoothing filters where an amount of smoothing for each smoothing filter is determined by a scale, and the plurality of filters includes a set of scales;
      b) finding a calcification response at each voxel of the reconstructed three-dimensional digital breast tomosynthesis image for each scale of the set of scales, where, among the set of scales, the calcification response at a central voxel of a three-dimensional microcalcification is higher when the scale is such that a shape of the smoothing filter approximately matches a shape of the three-dimensional microcalcification; and
      c) combining, among the set of scales, each calcification response using a non-linear operator at each voxel of the reconstructed three-dimensional digital breast tomosynthesis image; and
   detecting, at the computing device, potential individual microcalcifications that form a microcalcification cluster within the enhanced three-dimensional digital breast tomosynthesis image.

2. The computer-implemented method of claim 1, wherein detecting the seed object includes weighting a multi-scale calcification response volume for each voxel (x,y,z) by either: a) the signal-to-noise ratio enhanced three-dimensional digital breast tomosynthesis image or b) a signal intensity enhanced three-dimensional digital breast tomosynthesis image.

3. The computer-implemented method of claim 2, wherein the weighting creates an enhancement-modulated calcification response function at each voxel of the enhanced three-dimensional digital breast tomosynthesis image and the detected seed object includes a voxel having a value of the enhancement-modulated calcification response function that exceeds a threshold.

4. The computer-implemented method of claim 1, wherein detecting potential individual microcalcifications based on the location of the seed object includes:
   identifying a plurality of voxels within either: a) the signal-to-noise ratio enhanced three-dimensional digital breast tomosynthesis image or b) the signal intensity enhanced three-dimensional digital breast tomosynthesis image, wherein the identified plurality of voxels have a non-zero calcification response function; and iteratively identifying a subset of the plurality of identified voxels, wherein a signal-to-noise ratio value of each member of the subset is above a threshold.

5. The computer-implemented method of claim 1, wherein enhancing the signal-to-noise ratio of the microcalcification or enhancing the signal intensity of the microcalcification creates a three-dimensional enhancement-modulated calcification response image.

6. The computer-implemented method of claim 5, wherein determining the multi-scale calcification response for each voxel (x,y,z) of the microcalcification candidate includes, for the set of scales $\{\sigma\}$ surrounding the microcalcification candidate, the multi-scale calcification response at a voxel (x,y,z) defined as:

$$E(x, y, z) = \frac{r_{\sigma_{i*}}}{\sigma_{i*}},$$

wherein $r_{\sigma_{i*}}$ is a combined calcification response among all scales of the set of scales $\{\sigma\}$ and $\sigma_{i*}$ is the a combined scale ($\sigma$) of the set of scales $\{\sigma\}$.

7. A non-transitory computer-readable medium having instructions stored thereon, the instructions when executed by a processor detect a microcalcification cluster in reconstructed volumes of a three-dimensional digital breast tomosynthesis image, causing the processor to:

receive a three-dimensional digital breast tomosynthesis image;

reconstruct the three-dimensional digital breast tomosynthesis image to create a reconstructed three-dimensional digital breast tomosynthesis image;

enhance a microcalcification candidate in each slice of the reconstructed three-dimensional digital breast tomosynthesis image to obtain a three-dimensional enhancement-modulated calcification response image;

detect a seed object in the three-dimensional enhancement-modulated calcification response image, wherein the seed object includes a plurality of voxels; and detect a plurality of microcalcification candidates based on criteria including one or more of a proximity of each microcalcification candidate to the seed object and a signal-to-noise ratio value of each microcalcification candidate exceeding a threshold;

wherein the instruction to enhance the microcalcification candidate in each slice of the three-dimensional digital breast tomosynthesis image to obtain the three-dimensional enhancement-modulated calcification response image includes a multi-scale calcification response function to:

construct a Hessian matrix for each voxel of the reconstructed three-dimensional digital breast tomosynthesis image;

select a voxel of the reconstructed three-dimensional digital breast tomosynthesis image wherein all eigenvalues of the Hessian matrix corresponding to the selected voxel are negative;

determine a ratio between a square of a smallest magnitude eigenvalue and a negative value of a largest magnitude eigenvalue, wherein the ratio includes a calcification response;

create an enhanced three-dimensional digital breast tomosynthesis image by enhancing, for each voxel of the three-dimensional digital breast tomosynthesis image, either: a) a signal to noise ratio to obtain the enhanced three-dimensional digital breast tomosynthesis image or b) a signal intensity value to obtain the enhanced three-dimensional digital breast tomosynthesis image; and weight each voxel of a multi-scale calcification response volume by a value of either: a) the signal-to-noise ratio enhanced three-dimensional digital breast tomosynthesis image or b) the signal intensity value enhanced three-dimensional digital breast tomosynthesis image to obtain the three-dimensional enhancement-modulated calcification response image from the three-dimensional digital breast tomosynthesis image.

8. A computer system for detecting a microcalcification cluster in reconstructed volumes of a three-dimensional digital breast tomosynthesis image, the system comprising:

a processor;

a memory;

a reconstruction module stored in the memory and executed by the processor to reconstruct the three-dimensional digital breast tomosynthesis image to create a reconstructed three-dimensional digital breast tomosynthesis image;

an enhancement module stored in the memory and executed by the processor to enhance a microcalcification candidate in each slice of the reconstructed three-dimensional digital breast tomosynthesis image to obtain a three-dimensional enhancement-modulated calcification response image;

a seed detection module stored in the memory and executed by the processor to detect a seed object in the three-dimensional enhancement-modulated calcification response image, wherein the seed object includes a plurality of voxels;

a microcalcification candidate detection module stored in the memory and executed by the processor to detect a plurality of microcalcification candidates based on criteria including one or more of a proximity of each microcalcification candidate to the seed object and a signal-to-noise ratio value of each microcalcification candidate exceeding a threshold;

a multi-scale calcification response module stored in the memory and executed by the processor to obtain a multi-scale calcification response volume from a reconstructed volume of the three-dimensional digital breast tomosynthesis image by applying a multi-scale calcification response function to each voxel of the reconstructed volume, wherein the multi-scale calcification response function is configured to:

smooth the enhanced reconstructed three-dimensional digital breast tomosynthesis image;

construct a Hessian matrix for each voxel of the enhanced three-dimensional digital breast tomosynthesis image;

select a voxel of the enhanced three-dimensional digital breast tomosynthesis image wherein all eigenvalues of the Hessian matrix corresponding to the selected voxel are negative; and determine a ratio between a square of a smallest magnitude eigenvalue and a negative value of a largest magnitude eigenvalue, wherein the ratio includes a calcification response;

create an enhanced three-dimensional digital breast tomosynthesis image by enhancing, for each voxel of the three-dimensional digital breast tomosynthesis image, either: a) a signal to noise ratio to obtain the enhanced three-dimensional digital breast tomosynthesis image or b) a signal intensity value to obtain the enhanced three-dimensional digital breast tomosynthesis image; and a weighting module stored in the memory and executed by the processor to weight each voxel of the three-dimensional multi-scale calcification response volume by a value of either: a) the signal-to-noise ratio enhanced three-dimensional digital breast tomosynthesis image or b) the signal intensity value enhanced three-dimensional digital breast tomosynthesis image to obtain the three-dimensional enhancement-modulated calcification response image from the three-dimensional digital breast tomosynthesis image.

9. The computer system of claim 8, wherein the weighting module is further executed by the processor to weight the multi-scale calcification response volume by the signal-to-noise enhanced volume according to an equation:

$$EMCR(x, y, z) = E(x, y, z) * [I(x, y, z) \otimes F(x, y, z)]$$
where $I(x, y, z) \otimes F(x, y, z)$ denotes the signal-to-noise enhanced volume and $E(x, y, z)$ denotes the multi-scale calcification response volume.

10. A computer-implemented method for determining a strength of a microcalcification candidate in an image for differentiation of true and false microcalcifications comprising:

receiving an image including one of a two-dimensional projection view or a three-dimensional digital breast tomosynthesis slice image;

identifying a region of interest within the image including a plurality of microcalcification candidates;

characterizing the region of interest as a vector g including a set of channel response $\{g_1, \ldots, g_N\}$ given a multi-channel set;

differentiating each of the plurality of microcalcification candidates as one of a true microcalcification or a false microcalcification according to a linear classification model:

$$D(g) = (\overline{m_2} - \overline{m_1})^T \Sigma^{-1} g$$

wherein $\overline{m_k}$ includes a mean vector for class k where k=1,2, $\Sigma$ includes a covariance matrix estimated from training samples of true microcalcifications and false microcalcifications, and $D(g)$ includes a multi-channel enhancement (MCE) response representing the strength of each of the plurality of microcalcification candidates.

11. The computer-implemented method of claim 10, comprising using the MCE response to differentiate true and false microcalcifications and generating a measure of the microcalcification cluster including a cluster likelihood score (CLS), a level of suspicion (LOS), and an overall cluster significance rating (CSR).

12. The computer-implemented method of claim 11, further comprising estimating the CSR for each plurality of microcalcification candidates by:

extracting a plurality of features from the three-dimensional digital breast tomosynthesis image;

extracting the MCE response for each plurality of microcalcification candidates;

combining the extracted features and the MCE response into a CLS score by using a classifier trained to classify the detected plurality of microcalcification candidates as one of true or false;

combining the extracted features and the MCE response into a LOS score by using a classifier trained to classify the detected plurality of microcalcification candidates as one of malignant or benign;

weighting the CLS value by the LOS score.

13. A non-transitory computer-readable medium having instructions stored thereon, the instructions when executed by a processor determine a strength of a microcalcification candidate in an image for differentiation of true and false microcalcifications, causing the processor to:

receive an image including one of a two-dimensional projection view or a three-dimensional digital breast tomosynthesis slice image;

identify a region of interest within the image including a plurality of microcalcification candidates;

characterize the region of interest as a vector g including a set of channel response $\{g_1, \ldots, g_N\}$ given a multi-channel set;

differentiate each microcalcification candidate as one of a true microcalcification or a false microcalcification according to a linear classification model:

$$D(g) = (\overline{m_2} - \overline{m_1})^T \Sigma^{-1} g$$

wherein $\overline{m_k}$ includes a mean vector for class k where k=1,2, $\Sigma$ includes a covariance matrix estimated from training samples of true microcalcifications and false microcalcifications, and $D(g)$ includes a multi-channel enhancement (MCE) response representing the strength of each microcalcification candidate.

14. The non-transitory computer-readable medium of claim 13, further comprising instructions that, when executed by a processor, cause the processor to estimate a cluster significance rating (CSR) for each microcalcification candidate by:

extracting a plurality of features from the three-dimensional digital breast tomosynthesis image;

extracting the MCE response for each microcalcification candidate;

combining the extracted features and the MCE response into a CLS score by using a classifier trained to classify the detected plurality of microcalcification candidates as true or false;

combining the extracted features and the MCE response into a LOS score by using a classifier trained to classify the detected plurality of microcalcification candidates as malignant or benign;

weighting the CLS value by the LOS.

15. A computer system for determining a strength of a microcalcification candidate in an image for differentiation of true and false microcalcifications, the system comprising:

a processor;

a memory;

a receiving module stored in the memory and executed by the processor to receive an image including one of a two-dimensional projection view or a three-dimensional digital breast tomosynthesis slice image;

a prescreening module stored in the memory and executed by the processor to identify a region of interest within the image including a plurality of microcalcification candidates;

a vector module stored in the memory and executed by the processor to characterize the region of interest as a vector g including a set of channel response $\{g_1, \ldots, g_N\}$ given a multi-channel set;

a differentiation module stored in the memory and executed by the processor to differentiate each microcalcification candidate as one of a true microcalcification or a false microcalcification according to a linear classification model:

$$D(g) = (\overline{m_2} - \overline{m_1})^T \Sigma^{-1} g$$

wherein $\overline{m_k}$ includes a mean vector for class k where k=1,2, $\Sigma$ includes a covariance matrix estimated from training samples of true microcalcifications and false microcalcifications, and D(g) includes a multi-channel enhancement (MCE) response representing the strength of each microcalcification candidate.

16. The computer system of claim 15, further comprising a cluster significance rating (CSR) estimation module stored in the memory and executed by the processor to estimate the CSR for each microcalcification candidate by:
    extracting a plurality of features from the three-dimensional digital breast tomosynthesis image;
    extracting the MCE response for each microcalcification candidate;
    combining the extracted features and the MCE response into a CLS score by using a classifier trained to classify the detected plurality of microcalcification candidates as true or false;
    combining the extracted features and the MCE response into a LOS score by using a classifier trained to classify the detected plurality of microcalcification candidates as malignant or benign;
    weighting the CLS value by the LOS.

17. A computer-implemented method for detecting a microcalcification cluster in an image, comprising:
    enhancing, at a computing device, a received image, the image including one of a two-dimensional projection view or a three-dimensional digital tomosynthesis slice image and a plurality of microcalcification candidates, the enhancing including differentiating each of the plurality of microcalcification candidates as one of a true microcalcification or a false microcalcification according to a linear classification model:

$$D(g) = (\overline{m_2} - \overline{m_1})^T \Sigma^{-1} g$$

wherein $\overline{m_k}$ includes a mean vector for class k where k=1,2, $\Sigma$ includes a covariance matrix estimated from training samples of true microcalcifications and false microcalcifications, and D(g) includes a multi-channel enhancement (MCE) response representing a strength of each of the plurality of microcalcification candidates;
    back-projecting, at the computing device, an MCE-response for each microcalcification candidate on the two-dimensional projection view to the three-dimensional tomosynthesis image
    determining, at the computing device, a multi-scale calcification response function for the three-dimensional tomosynthesis image by:
        smoothing the enhanced reconstructed three-dimensional digital breast tomosynthesis image;
        constructing a Hessian matrix for each voxel of the enhanced reconstructed three-dimensional digital breast tomosynthesis image;
        selecting a voxel of the enhanced reconstructed three-dimensional digital breast tomosynthesis image wherein all eigenvalues of the Hessian matrix corresponding to the selected voxel are negative; and
        determining a ratio between a square of a smallest magnitude eigenvalue and a negative value of a largest magnitude eigenvalue, wherein the ratio includes a calcification response;
    weighting, at the computing device, the multi-scale calcification response volume by the back-projected MCE-response;
    detecting, at the computing device, a seed object in the weighted multi-scale calcification response volume.

18. A non-transitory computer-readable medium having non-transitory instructions stored thereon, the instructions when executed by a processor detect a microcalcification cluster in an image, causing the processor to:
    enhance a received image, the image including one of a two-dimensional projection view or a two-dimensional digital tomosynthesis slice image and a plurality of microcalcification candidates, the enhance instruction further causing the processor to differentiate each of the plurality of microcalcification candidates as one of a true microcalcification or a false microcalcification according to a linear classification model:

$$D(g) = (\overline{m_2} - \overline{m_1})^T \Sigma^{-1} g$$

wherein includes a mean vector for class k where k=1,2, includes a covariance matrix estimated from training samples of true microcalcifications and false microcalcifications, and D(g) includes a multi-channel enhancement (MCE) response representing a strength of each of the plurality of microcalcification candidates;
    back-project an MCE-response for each microcalcification candidate on the two-dimensional projection view to the three-dimensional tomosynthesis image
    determine a multi-scale calcification response function for the three-dimensional tomosynthesis image by:
        smoothing the enhanced reconstructed three-dimensional digital breast tomosynthesis image;
        constructing a Hessian matrix for each voxel of the enhanced reconstructed three-dimensional digital breast tomosynthesis image;
        selecting a voxel of the enhanced reconstructed three-dimensional digital breast tomosynthesis image wherein all eigenvalues of the Hessian matrix corresponding to the selected voxel are negative; and
        determining a ratio between a square of a smallest magnitude eigenvalue and a negative value of a largest magnitude eigenvalue, wherein the ratio includes a calcification response;
    weight the multi-scale calcification response volume by the back-projected MCE-response;
    detect a seed object in the weighted multi-scale calcification response volume, wherein the seed object includes a plurality of voxels.

19. A computer system for detecting a microcalcification cluster in an image, the system comprising:
    a processor;
    a memory;
    a two-dimensional image enhancement module stored in the memory and executed by the processor to enhance a received image, the image including one of a two-dimensional projection view or a two-dimensional digital tomosynthesis slice image and a plurality of microcalcification candidates, the two-dimensional image enhancement module further differentiating each of the plurality of microcalcification candidates as one of a true microcalcification or a false microcalcification according to a linear classification model:

$$D(g) = (\overline{m_2} - \overline{m_1})^T \Sigma^{-1} g$$

wherein $\overline{m_k}$ includes a mean vector for class k where k=1,2, $\Sigma$ includes a covariance matrix estimated from training samples of true microcalcifications and false microcalcifications, and D(g) includes a multi-channel enhancement (MCE) response representing a strength of each of the plurality of microcalcification candidates;

a seed object detection module stored in the memory and executed by the processor to:
  back-project an MCE-response for each microcalcification candidate on the two-dimensional projection view to the three-dimensional tomosynthesis image
  determine a multi-scale calcification response function for the three-dimensional tomosynthesis image by:
    smoothing the enhanced reconstructed three-dimensional digital breast tomosynthesis image;
    constructing a Hessian matrix for each voxel of the enhanced reconstructed three-dimensional digital breast tomosynthesis image;
    selecting a voxel of the enhanced reconstructed three-dimensional digital breast tomosynthesis image wherein all eigenvalues of the Hessian matrix corresponding to the selected voxel are negative; and
    determining a ratio between a square of a smallest magnitude eigenvalue and a negative value of a largest magnitude eigenvalue, wherein the ratio includes a calcification response;
  weight the multi-scale calcification response volume by the back-projected MCE-response; and
  detect a seed object in the weighted multi-scale calcification response volume
a clustering module stored in the memory and executed by the processor to detect a microcalcification cluster based on a location of the seed object in the weighted multi-scale calcification response volume, the microcalcification cluster having a plurality of microcalcification candidates with a calcification response above a threshold.

* * * * *